(12) United States Patent
Kim et al.

(10) Patent No.: US 11,751,762 B2
(45) Date of Patent: Sep. 12, 2023

(54) METHOD AND APPARATUS FOR LOW COHERENCE INTERFEROMETRY

(71) Applicant: Topcon Corporation, Tokyo (JP)

(72) Inventors: Jongsik Kim, Fort Lee, NJ (US); Ying Dong, Warren, NJ (US); Song Mei, Franklin Park, NJ (US); Kinpui Chan, Ridgewood, NJ (US); Zhenguo Wang, Ridgewood, NJ (US); Zaixing Mao, Edgewater, NJ (US)

(73) Assignee: TOPCON CORPORATION, Tokyo (JP)

( * ) Notice: Subject to any disclaimer, the term of this patent is extended or adjusted under 35 U.S.C. 154(b) by 744 days.

(21) Appl. No.: 16/719,305

(22) Filed: Dec. 18, 2019

(65) Prior Publication Data

US 2020/0196856 A1    Jun. 25, 2020

Related U.S. Application Data

(60) Provisional application No. 62/822,415, filed on Mar. 22, 2019, provisional application No. 62/781,991, filed on Dec. 19, 2018.

(51) Int. Cl.
*A61B 3/10* (2006.01)
*A61B 3/14* (2006.01)
(Continued)

(52) U.S. Cl.
CPC .......... *A61B 3/102* (2013.01); *A61B 3/1225* (2013.01); *A61B 3/14* (2013.01); *G01N 21/17* (2013.01); *G01N 2021/1787* (2013.01)

(58) Field of Classification Search
CPC ......... A61B 3/14; A61B 3/102; A61B 3/1225; A61B 3/1241; G01B 9/02091; G01B 9/02094; G01N 21/17; G01N 2021/1787
See application file for complete search history.

(56) References Cited

U.S. PATENT DOCUMENTS

| 2016/0317018 A1 | 11/2016 | Sakagawa |
| 2016/0317029 A1 | 11/2016 | Srivastava et al. |
| 2017/0360294 A1 | 12/2017 | Satake et al. |

OTHER PUBLICATIONS

Extended European Search Report for European Patent Application No. 19218145.1 dated May 18, 2020.
(Continued)

*Primary Examiner* — Jack Dinh
(74) *Attorney, Agent, or Firm* — Pearne & Gordon LLP

(57) ABSTRACT

A low coherence imaging method comprises acquiring image data of an object with an interferometric imaging system, where the image data is from a location of the object at first and second times; determining a first depth profile from the image data from the location at the first time and a second depth profile from the image data of the location at the second time; determining a change with respect to depth between the first and second depth profiles; and determining a property, or identifying a location, of at least one dynamic particle in the object based on the change between the first and second depth profiles. The method is able to identify, analyze, and/or visualize dynamic particles with features comparable to at least fluorescein angiography, indocyanine green angiography, confocal scanning laser fluorescein angiography, confocal scanning laser indocyanine green angiography, and fluorescence microscopy images, without the use of a dye.

19 Claims, 24 Drawing Sheets

Color Fundus

2D Projection – Dynamic Particle Counting

(51) Int. Cl.
*A61B 3/12* (2006.01)
*G01N 21/17* (2006.01)

(56) References Cited

OTHER PUBLICATIONS

Boas et al., "Laser speckle contrast imaging in biomedical optics"; Journal of Biomedical Optics; vol. 15(1), pp. 011109-1-011109-12; Jan./Feb. 2010.

Briers et al., "Laser speckle contrast imaging: theoretical and practical limitations", Journal of Biomedical Optics, vol. 18(6), 066018, Jun. 2018.

Choi et al., "Improved microcirculation imaging of human skin in vivo using optical microangiography with a correlation mapping mask"; Journal of Biomedical Optics, vol. 19(3), 036010, pp. 1-10, Mar. 2014.

Fingler et al., "Mobility and transverse flow visualization using phase variance contrast with spectral domain optical coherence tomography"; Optics Express 12636, vol. 15, No. 20, pp. 1-18, Oct. 1, 2007.

Fingler et al., "Volumetric microvascular imaging of human retina using optical coherence tomography with a novel motion contrast technique", Optics Express 22191, vol. 17, No. 24, pp. 1-11, Nov. 23, 2009.

Glittenberg et al., "Introduction to swept source optical coherence tomography angiography"; Angie-OCT / Medical Retina, pp. 1-18, Aug. 23, 2017.

Hendargo et al., "Automated non-rigid registration and mosaicing for robust imaging of distinct retinal capillary beds using speckle variance optical coherence tomography", Biomedical Optics Express, vol. 4, No. 6, Jun. 1, 2013.

Jia et al., "Split-spectrum amplitude-decorrelation angiography with optical coherence tomography", Optics Express 1710, vol. 20, No. 4, pp. 1-16, Feb. 13, 2012.

Makita et al., "Comprehensive in vivo micro-vascular imaging of the human eye by dual-beam-scan Doppler optical coherence angiography", Optics Express 1271, vol. 19, No. 2, Jan. 17, 2011, pp. 1-13.

Mariampillai et al., "Speckle variance detection of microvasculature using swept-source optical coherence tomography", Optics Letters, vol. 33, No. 13, pp. 1530-1532, Jul. 1, 2008.

Motaghiannezam et al., "Logarithmic intensity and speckle-based motion contrast methods for human retinal vasculature visualization using swept source optical coherence tomography", Biomedical Optics Express 503, vol. 3, No. 3, pp. 1-19, Mar. 1, 2012.

Ruminski et al., "Angiogram visualization and total velocity blood flow assessment based on intensity information analysis of OCT data", Optical Coherence Tomography and Coherence Domain Optical Methods in Biomedicine XVI, Proc. of SPIE vol. 8213, pp. 1-7, May 19, 2015.

Schmoll et al., "Imaging of the parafoveal capillary network and its integrity analysis using fractal dimension", Biomedical Optics Express, vol. 2, No. 5, pp. 1159-1168, May 1, 2011.

Spaide et al., "Optical coherence tomography angiography", Prog Retin Eye Res., pp. 1-161, Mar. 7, 2019.

Srinivasan et al., "Rapid volumetric angiography of cortical microvasculature with optical coherence tomography", Optics Letters, vol. 35, No. 1, pp. 43-45, Jan. 1, 2010.

Xu et al., "Real-time acquisition and display of flow contrast using speckle variance optical coherence tomography in a graphics processing unit", Journal of Biomedical Optics, vol. 19, No. 2, pp. 1-6, Feb. 2014.

Zotter, et al., "Visualization of microvasculature by dual-beam phase-resolved Doppler optical coherence tomography", Optics Express, vol. 19, No. 2, pp. 1217-1227, Jan. 17, 2011.

METHOD AND APPARATUS FOR LOW COHERENCE INTERFEROMETRY

CROSS-REFERENCE TO RELATED APPLICATIONS

This application claims priority to U.S. Provisional Application Ser. No. 62/781,991, filed on Dec. 19, 2018, entitled "METHOD AND APPARATUS FOR LOW COHERENCE INTERFEROMETRY"; and to U.S. Provisional Application Ser. No. 62/822,415, filed on Mar. 22, 2019, entitled "METHOD AND APPARATUS FOR LOW COHERENCE INTERFEROMETRY"; the entireties of which are incorporated herein by reference.

BACKGROUND

There are currently different medical imaging modalities and techniques for measuring and visualizing dynamic speckles/particles (herein, the terms "speckle" and "particle" are used interchangeably). For example, such dynamic speckles/particles may be those that change size, shape, location, and the like. One example modality, optical coherence tomography (OCT) angiography (OCT-A), utilizes the reflectance of a laser light from the surface of moving red blood cells to depict vessels through different segmented areas/depths of an imaging sample. An example OCT angiography image is shown in FIG. 1. OCT angiography images have a contrast that is proportional to the intensity of backscattered light from the imaging sample. The intensity of backscattered light is a function of the optical properties of the moving speckles/particles illuminated by the incident laser light. These moving speckles/particles may include red blood cells, white blood cells, platelets, and the like.

FIG. 2 illustrates an example laser speckle contrast image. Laser speckle contrast imaging generates images having a contrast that is proportional to a fluid flow or fluid movement, or that is proportional to the velocity of a moving speckle. Still another example, dynamic light scattering (DLS), is shown in FIG. 3. Dynamic light scattering is used to determine the size distribution profile of small speckles in suspension or polymers in solution. Temporal fluctuations are usually determined by analyzing the intensity or photon auto-correlation function (ACF), or power spectrum.

SUMMARY OF THE INVENTION

According to one example herein, an imaging method comprises: acquiring an image data set of an object with an interferometric imaging system, wherein the image data set comprises image data from a location of the object at a first time and at a second time; determining a first depth profile from the image data from the location at the first time and a second depth profile from the image data of the location at the second time; determining a change with respect to depth between the first depth profile and the second depth profile; and determining a property, or identifying a location, of at least one dynamic particle in the object based on the change between the first depth profile and the second depth profile.

In various embodiments of the above example, the method further comprises generating an image of the object based on the at least one determined dynamic particle property, and displaying the image; the first depth profile or the second depth profile is in the complex domain; a light source of the interferometric imaging system is a low coherence light source; the change is a difference between the first depth profile and the second depth profile, or an absolute value of the difference; the change is a ratio between the first depth profile and the second depth profile, or an absolute value of the ratio; the change is a correlation or decorrelation between the first depth profile and the second depth profile; the change is a standard deviation or variance between the first depth profile and the second depth profiles; the method further comprises identifying depths of the object at which the change between the first depth profile and the second depth profile is at a local maxima or minima, wherein the identified depths correspond to locations of dynamic particles; the method further comprises determining a first derivative of the change between the first depth profile and the second depth profile, and identifying depths of the object at which the first derivative is zero, wherein the identified depths correspond to locations of dynamic particles; the method further comprises determining a first derivative of the change between the first depth profile and the second depth profile, and identifying depths of the object at which the first derivative is not zero, wherein the property of the at least one dynamic particle is based on a number of identified depths; the method further comprises applying a threshold to the first depth profile and/or the second depth profile prior to determining the change between the first depth profile and the second depth profile; the method further comprises applying a threshold to the change between the first depth profile and the second depth profile prior to generating the image; the threshold is: proportional to a noise floor of the interferometric imaging system, determined from a histogram or a cumulative histogram of an intensity of the first depth profile or the second depth profile, or is proportional to a frame size and/or sample size of the image data; the threshold is: proportional to a noise floor of the interferometric imaging system, determined from a histogram of a difference level of the change between the first depth profile and the second depth profile, or is proportional to a frame size and/or sample size of the image data; the image data set is 3D optical coherence tomography data; the object is a human eye; the determined property is a dynamic particle density, and the dynamic particle density is determined as the total number of identified locations of dynamic particles over a predefined depth within a region of interest; the determined property is a size of the at least one dynamic particle, and the size is proportional to a width of a local maxima or minima peak of the change between the first depth profile and the second depth profile, or to a distance between depths at which a first derivative of the change between the first depth profile and the second depth profile is zero; the method further comprises determining a dynamic particle size distribution based on the determined sizes; and/or the method further comprises determining a power spectrum of a first derivative of the change between the first depth profile and the second depth profile.

DETAILED DESCRIPTION

The above-described OCT-A, laser speckle contrast imaging, and DLS techniques, however, suffer from various limitations. For example, OCT-A image contrast is proportional to the optical property of a given speckle, not the local dynamic speckle concentration and/or dimension. Further, stronger optical scattering caused by the imaged speckles causes higher intensity (or amplitude) in a resulting measured OCT-A signal. Thus, weakly scattering speckles are less visible (or have a lower signal-to-noise ratio) in a measured OCT-A signal. Similarly, slowly moving speckles are less visible in a measured laser speckle contrast signal (or image). In DLS, the optical beam is stationary relative to sample such that the scattering speckles move relative to optical beam. Additionally, there is no depth profile in DLS.

The present disclosure relates to a low coherence interferometry method and apparatus able to determine, analyze, and/or visualize dynamic speckles and that does not necessarily suffer from the above-noted limitations. Low coherence interferometry as described herein can provide imaging features comparable to fluorescein angiography (FA), indocyanine green angiography (ICGA), confocal scanning laser fluorescein angiography (CSL-FA), confocal scanning laser indocyanine green angiography (CSL-ICGA), and fluorescence microscopy (FM) images, which have a contrast proportional to a dye contrast, the dye speckles flowing in a similar manner to those intended to be imaged. However, no dye is needed with low coherence interferometry. The conventional methods (e.g., OCT angiography, laser speckle contrast imaging, etc.) are unable to provide such features. With low coherence interferometry, the pixel intensity in an image (or signal strength at the pixel location) is proportional to local dynamic speckle concentration (or density) and/or dimension. If an image (or signal) is from a tissue, low coherence interferometry as described herein can be used to reveal abnormalities in the tissue by showing the difference between healthy and diseased tissues.

Figure 1:
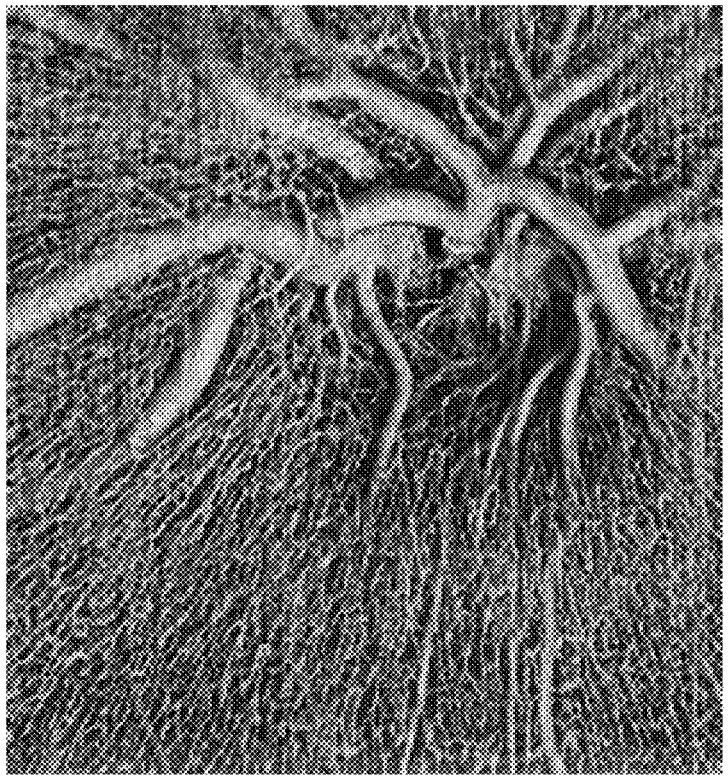
FIG. 1 illustrates an example optical coherence tomography angiography image.
Figure 2:
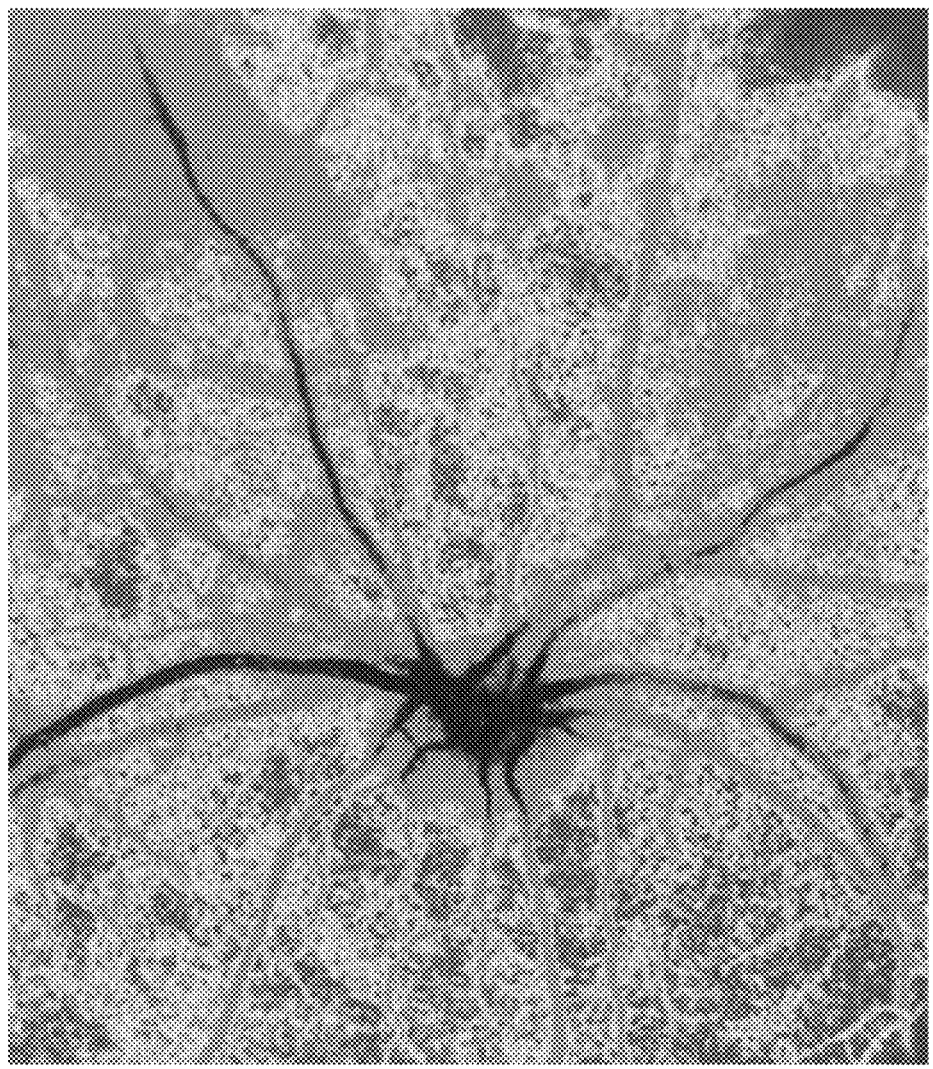
FIG. 2 illustrates an example laser speckle contrast image.
Figure 3:
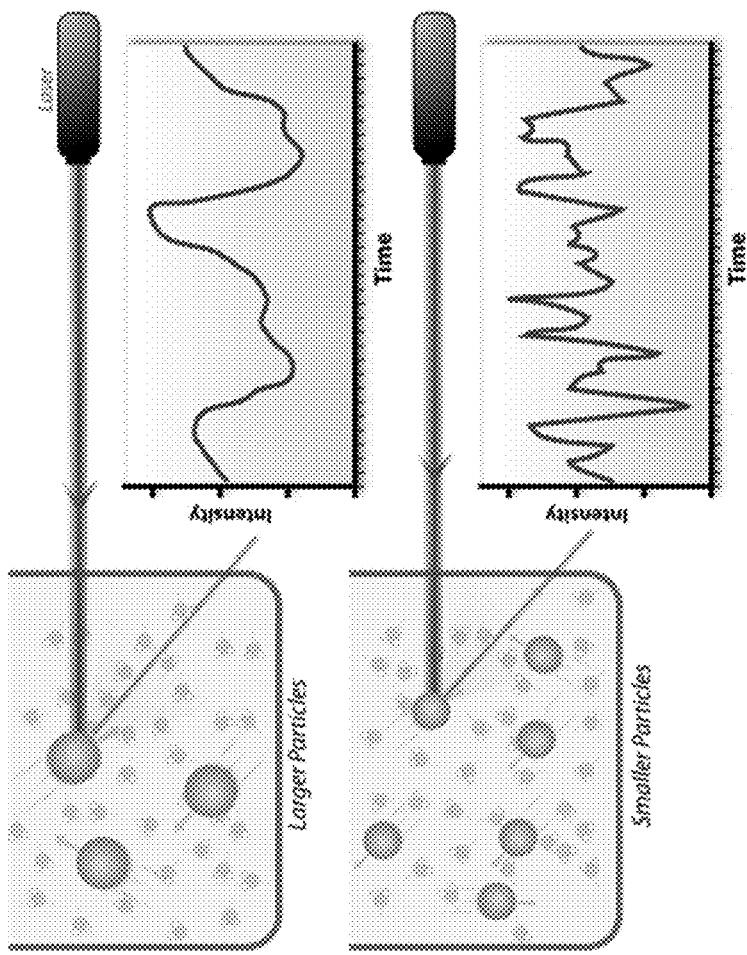
FIG. 3 illustrates an example of dynamic light scattering.
Figure 4:
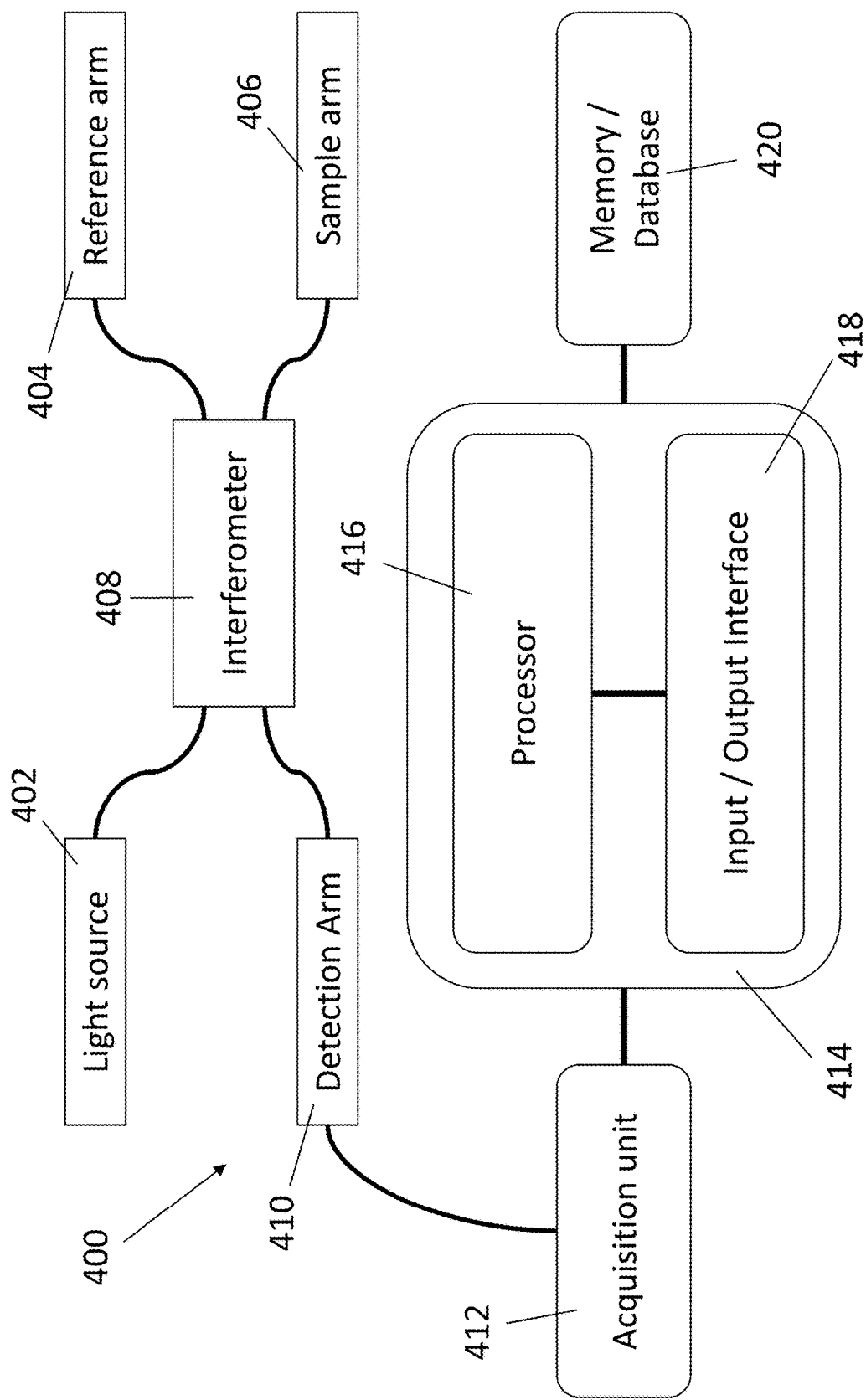
FIG. 4 illustrates an example schematic of a low coherence interferometry system of the present disclosure.

FIG. 4 illustrates an example schematic of a low coherence interferometry system 400. As with other interferometric modalities, the system herein includes a light source 402, reference arm 404, and sample arm 406. In this case the light source 402 is one that generates a low coherence length light. That light generated by the light source 402 is split by, for example, a beam splitter (as part of interferometer optics 408), and sent to the reference 404 and sample arms 406. Light is reflected by an object being imaged in the sample arm 406 and by a mirror in the reference arm 404. The reflected light from the reference 404 and sample arms 406 is then recombined in the detection arm 410 and detected by, for example, a photodetector therein.

The output of the photodetector is then supplied to an acquisition unit 412, such as a data acquisition unit and/or an analog-to-digital converter, which can then be provided to a computer or like system 414 having a processor 416 and an input/output interface 418. The processor 416 may be configured or otherwise programmed to analyze the data received by detector in the detection arm 410 and acquisition unit 412. The input/output interface 418 may include a display for outputting the processed images, or information relating to the analysis of those images. The input/output interface may also include any hardware such as buttons, keys, or other controls for receiving user inputs to the computer system 414.

The system 400 may also include memory for storing the images and analysis data. This information may be stored, for example, as part of a database 420. Additionally, the memory and/or database 420 may include reference data, such as a normative database. The data may be stored on local memory as part of computer system 414 or stored remotely, for example, on a separate server.

Figure 5:
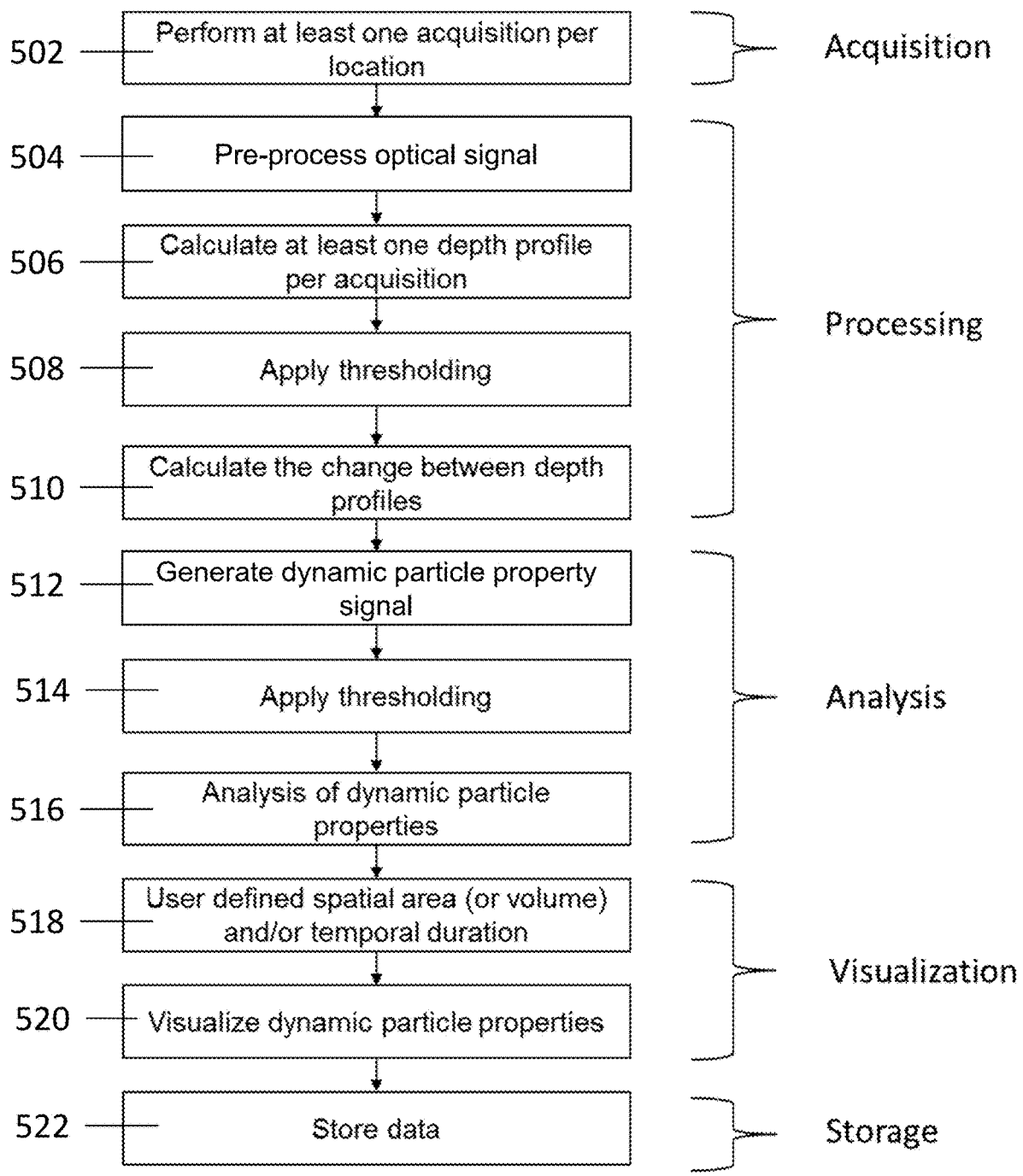
FIG. 5 illustrates an example workflow of the present disclosure.

An example workflow of the present disclosure is illustrated in FIG. 5. As seen therein, data is first acquired, then processed and analyzed, so that the analysis can finally be visualized (e.g., as the image or resulting analysis data) and stored (e.g., in the aforementioned database(s) 420). Acquisition involves acquiring imaging data 502 (e.g., an interfering optical signal) with the low coherence interferometry system 400 described above. Preferably, data is acquired at least one time at each location of interest of the object being imaged. Collectively this data may form, for example, a traditional 3D optical coherence tomography (OCT) dataset. In such cases, the low coherence interferometry system 400 may be an OCT system.

The acquired data is next processed, for example, by the processor 416 of the above-described system 400 in order to reconstruct a depth profile of each location at each time data was acquired from that location. This can first include pre-processing 504 the acquired optical signal data, for example, by filtering the signal to remove any white noise and/or numerically compensating for optical dispersion. Pre-processing 504 may also include converting signal measurements in the wavelength domain to the wavenumber domain and then, optionally, numerically resampling the signal after the conversion.

Figure 6A:
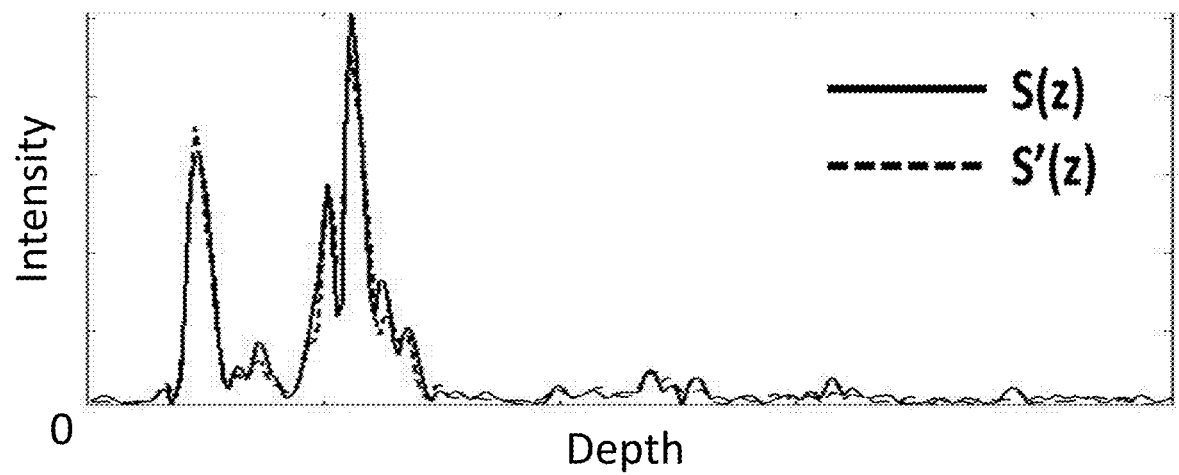
FIG. 6A illustrates two example depth profiles taken from a same location at different times.

Next, the depth profile of the data at each location at each time of acquisition is determined 506. The depth profile can be reconstructed by taking the Fourier transform or the non-uniform Fourier transform of the (pre-processed) optical signal (or optical signal converted to the wavenumber domain), or non-preprocessed acquired signal. The depth profile may also be reconstructed by using other like transforms, and may be in the complex domain or the real domain. In some embodiments, multiple depth profiles can be reconstructed from a single optical signal. Comparing depth profiles from the same location at two different times, the change between the depth profiles can be calculated 510. Example depth profiles are illustrated in FIG. 6A from imaging data of a human retina. There, two depth profiles $S(z)$ and $S'(z)$ taken from the same location at different times are shown as an acquired signal intensity over depth. The profiles may correspond to individual A-lines (e.g., from the 3D OCT dataset) and the depth may thus be represented as discrete depths corresponding to pixels of a 2D image (e.g., a B-scan) of a plurality of A-lines. The constructed depth profile may be in a form of complex numbers.

Figure 6B:
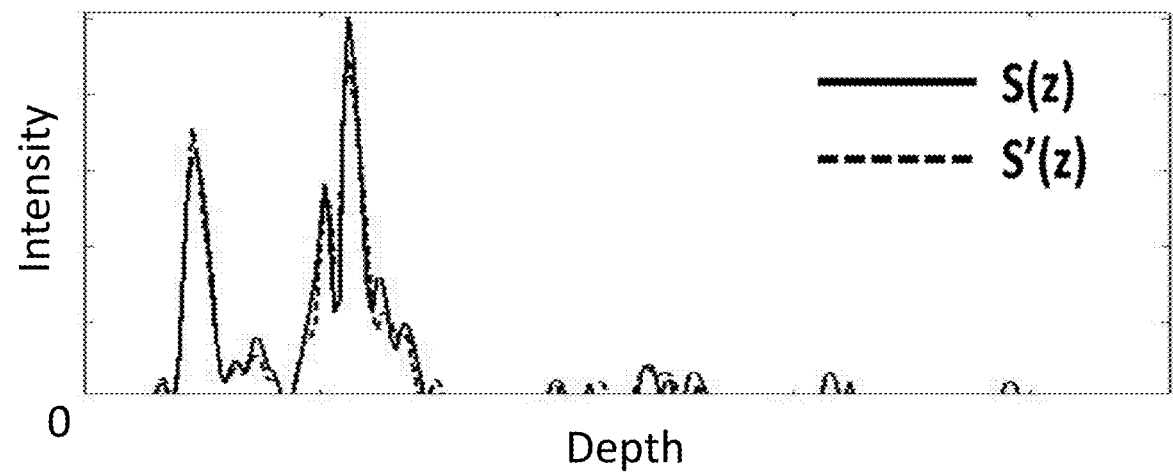
FIG. 6B illustrates the two example depth profiles of FIG. 6A after thresholding.

Referring back to FIG. 5, after constructing the depth profiles and/or calculating a change between depth profiles, a thresholding 508, 514 may then be optionally applied to the constructed depth profiles or their difference. The thresholding may, for example, act to remove a particular level of background noise so that only portions of the signal having an intensity at or above the threshold are considered. In this manner, the threshold may be a minimum intensity level of the depth profile. A result of an example applied threshold to the depth profiles $S(z)$ and $S'(z)$ shown in FIG. 6A, is illustrated in FIG. 6B. Therein it can be seen that low intensity noise is removed from the depth profile signals. Of course, in other embodiments, a threshold may additionally or alternatively be used to set maximum intensity levels of the depth profile.

Figure 7A:
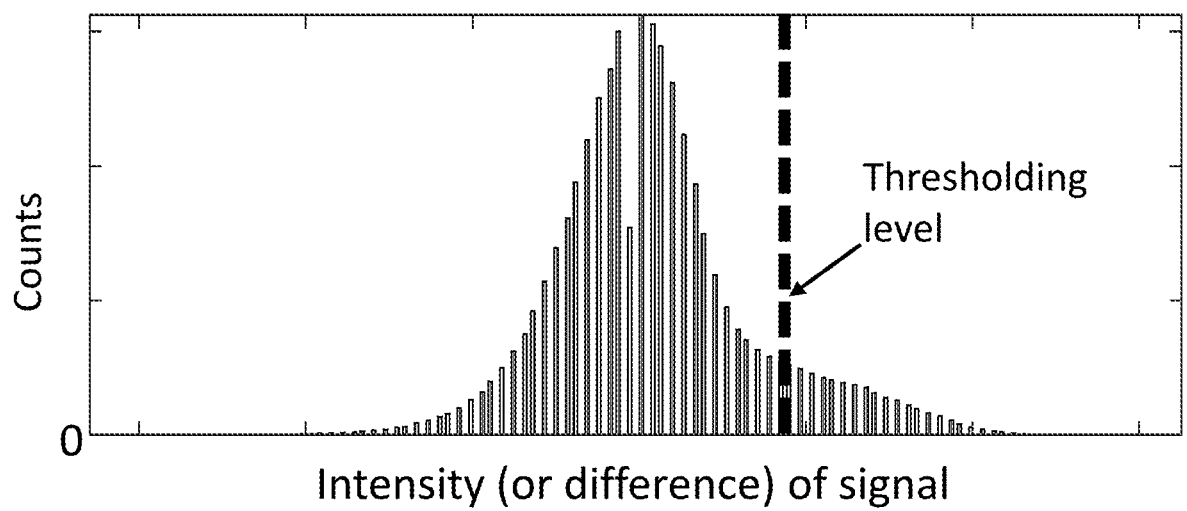
FIGS. 7A and 7B illustrate histograms of intensity levels of an optical signal for determining a threshold level.
Figure 7B:
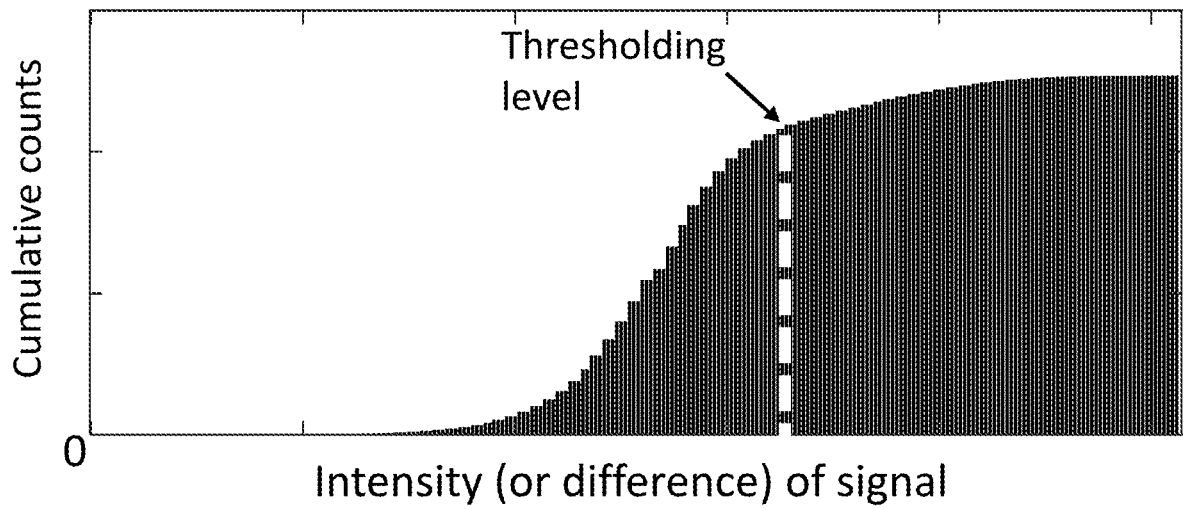

There are many ways to determine a thresholding level applied to the depth profiles. For example, the shape of a histogram (or like distribution) of intensity values of an OCT B-scan can be influenced by at least B-scan size, tissue size, and number of types of tissues, since these characteristics influence the relative pixel intensities of the B-scan image (and consequently, any differences between B-scans at corresponding locations taken at different times). FIG. 7A illustrates an example histogram of intensity levels for an optical signal of a B-scan. As shown therein, a thresholding level shown may thus be set based on the histogram to remove background noise (constituting a majority of the signal) and may be proportional to a signal-to-noise ratio (SNR) of the B-scan. In another embodiment illustrated in a cumulative histogram in FIG. 7B, the thresholding level is influenced by the B-scan size and/or sample size (e.g., tissue size). Therein, the threshold is set to an intensity below which most of the meaningful optical signal is found.

Figure 8:
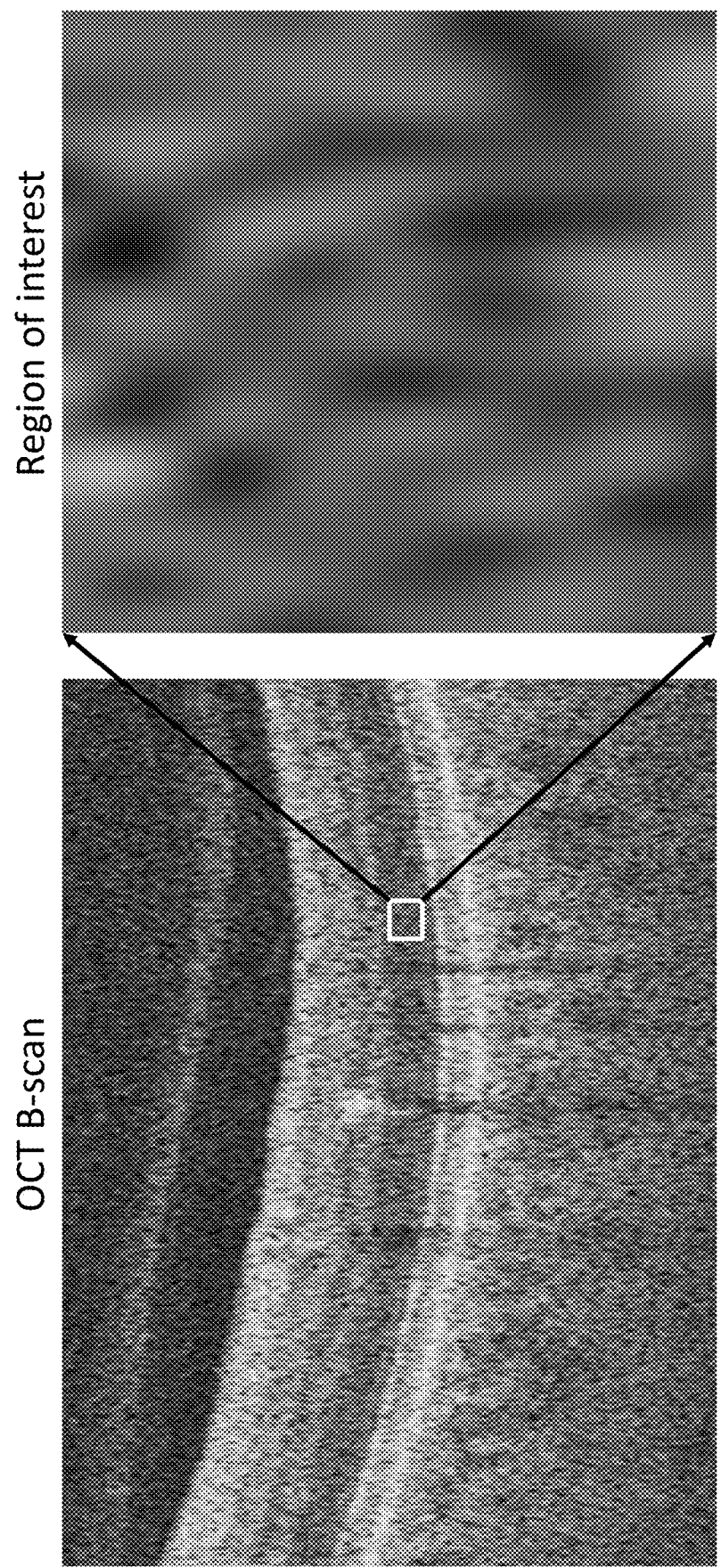
FIG. 8 illustrates the selection of a region of interest used for determining a threshold level.

In still another embodiment, the thresholding level can be proportional to a mean intensity of a region of interest of the object being imaged. As seen in FIG. 8, a region of interest is selected from an OCT B-scan image. Each pixel of the region of interest may be averaged to produce a mean intensity of the B-scan image, and a threshold may be selected as a proportional level relative to that mean intensity. In still other embodiments, the threshold may be proportional to any other statistical determinations (e.g., median intensity, standard deviation of intensity, and the like) and/or characteristics of the depth profiles, acquired imaging data, or the like.

Figure 9:
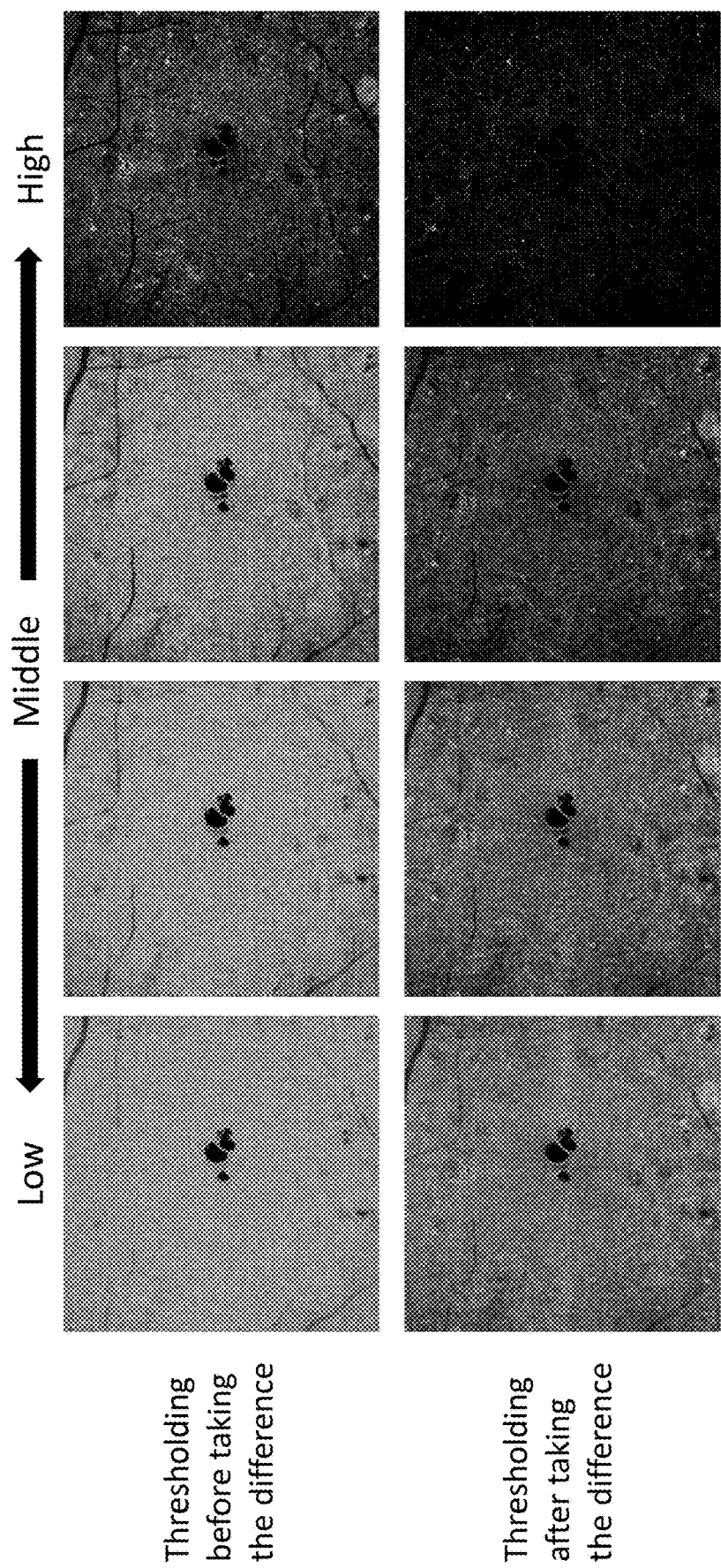
FIG. 9 illustrates the effects of different threshold level values when applied before and after determining a difference between depth profiles associated with each image.

FIG. 9 illustrates the effects of different threshold level values when applied before and after determining a difference between depth profiles associated with each image. As seen therein, the thresholding level helps visualize abnormalities in the imaged object. For example, at the extremes, it is seen that the highest intensity speckles are more clearly visible after applying the highest threshold levels. As noted above, the threshold process can be applied to the example depth profiles directly and/or to the change between the example depth profiles (e.g., as determined by taking a difference between the depth profiles).

Figure 10:
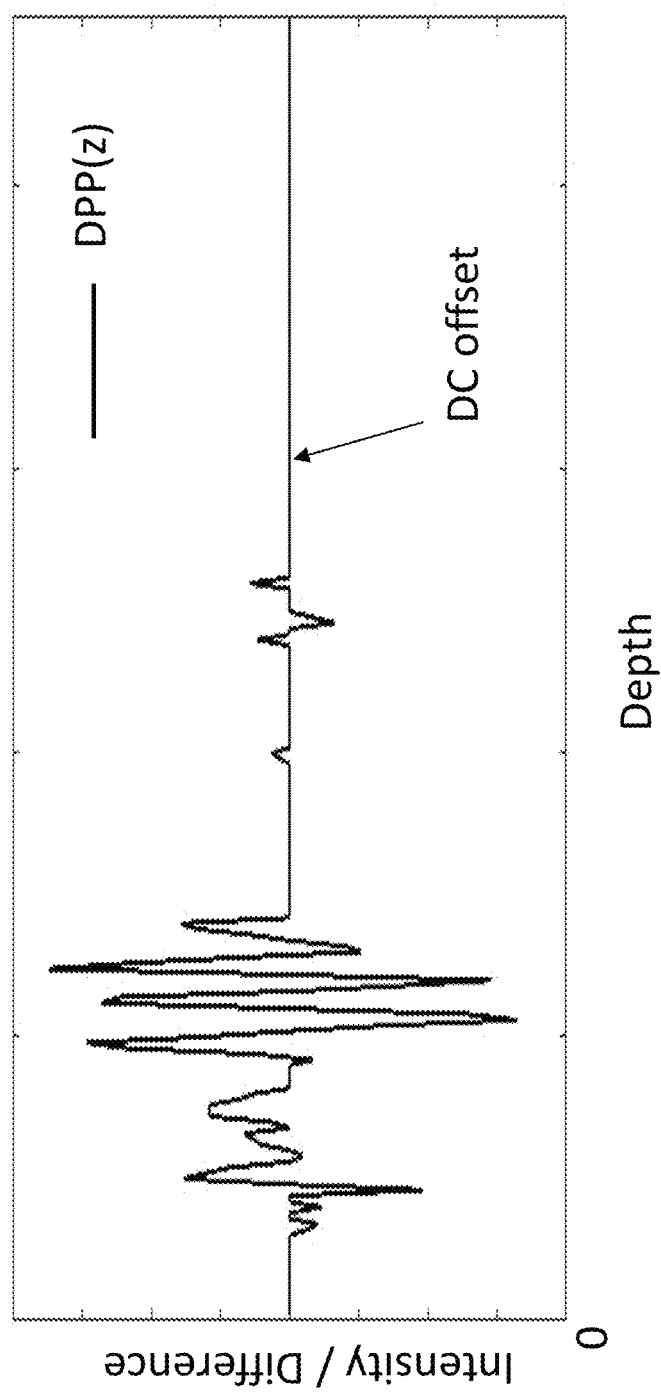
FIG. 10 illustrates an example dynamic speckle property signal DPP(z) based on the two thresholded depth profiles of FIG. 6B.

Referring back to FIG. 5, after constructing the depth profiles 506 and optionally applying a threshold 508 to the depth profile, the differences (or changes) between each depth profile are calculated 510 to generate a dynamic speckle property signal $DPP(z)$ 512. An example dynamic speckle property signal $DPP(z)$ is shown in FIG. 10, which is based on the two thresholded depth profiles shown in FIG. 6B. This change between depth profiles can be determined quantitatively using any numerical operation.

For example, the dynamic speckle property signal $DPP(z)$ may be equal to the numerical differences/changes (or the absolute value thereof) between depth profiles. In other words:

$$DPP(z) = S(z) - S'(z)$$

or $$DPP(z) = |S(z) - S'(z)|$$

The dynamic speckle property signal $DPP(z)$ is based on the numerical difference between the depth profiles $S(z)$ and $S'(z)$. According to another embodiment, the dynamic speckle property signal $DPP(z)$ may be equal to a ratio of the depth profiles (or the absolute value thereof). In other words:

$$DPP(z) = \frac{S(z)}{S'(z)}$$

or $$DPP(z) = \left|\frac{S(z)}{S'(z)}\right|$$

In still other embodiments, the generated dynamic speckle property signal $DPP(z)$ may be determined using any numerical method that considers differences between two elements. For example, the dynamic speckle property signal DPP(z) may be equal to or based on a correlation or decorrelation between a first depth profile and the second depth profile (e.g., S(z) and S'(z)), equal to or based on a standard deviation or variance between the depth profiles, or the like.

Figure 11A:
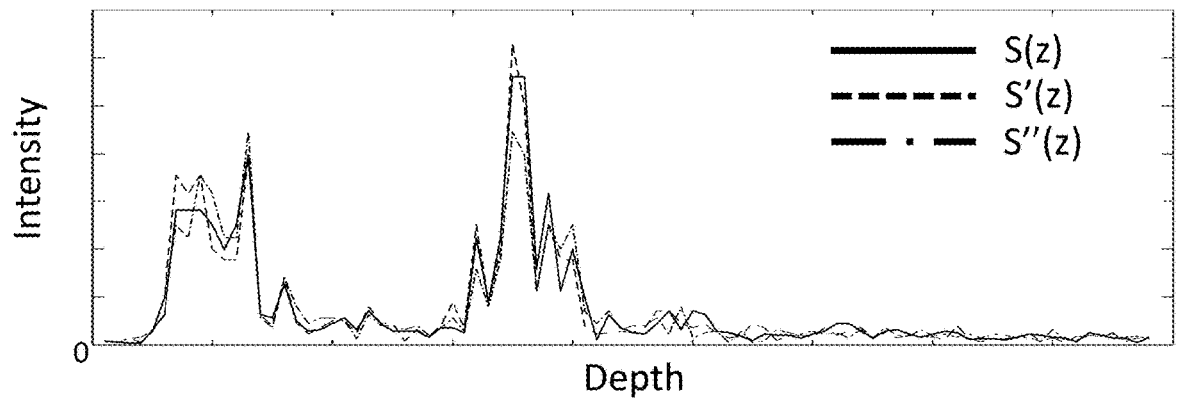
FIG. 11A illustrates three depth profiles S(z), S'(z), and S"(z) taken from the same location at different times.
Figure 11B:
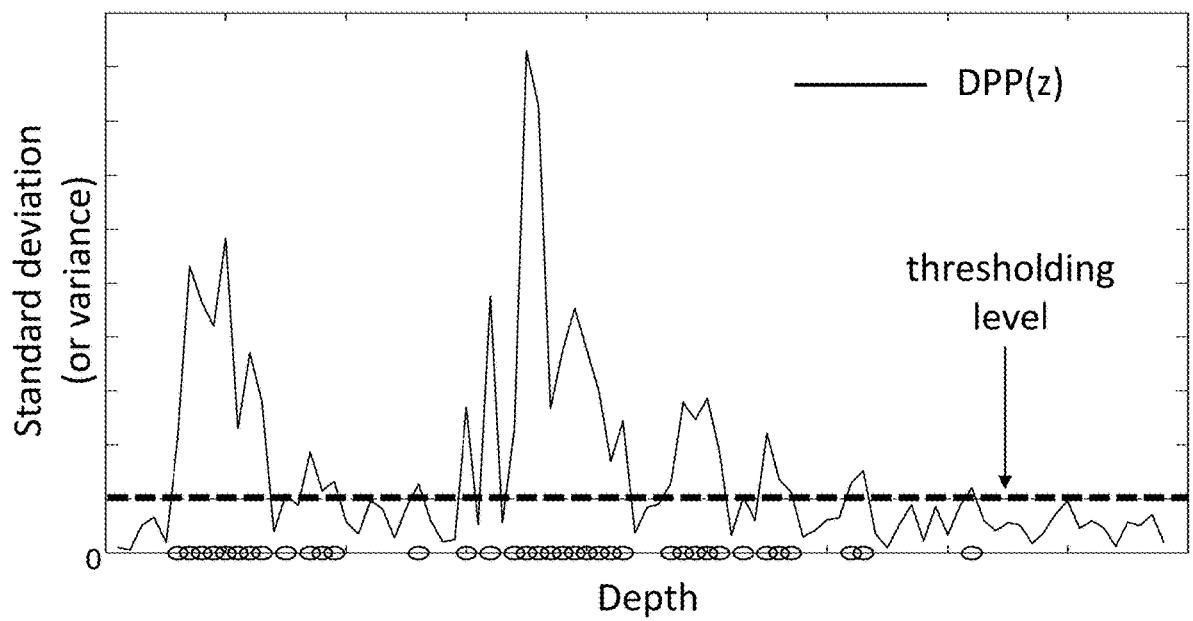
FIG. 11B illustrates an example dynamic speckle property signal DPP(z) as the standard deviation of the three depth profiles S(z), S'(z), and S"(z) of FIG. 11A.

For example, FIG. 11B illustrates an example of a dynamic speckle property signal DPP(z) based on a statistical standard deviation or variance between multiple depth profiles shown, each of which is illustrated in FIG. 11A. The three depth profiles S(z) and S'(z) and S"(z) in FIG. 11A are taken from the same location at different times are shown as an acquired signal intensity over depth. The differences (or change) between each profile can then be measured by calculating a statistical standard deviation or variance between each profile, the resulting dynamic speckle property signal being illustrated in FIG. 11B. As discussed above, a thresholding (e.g., a threshold standard deviation or variance level) 508, 514 may be applied to the depth profiles directly or to the dynamic speckle property signal DPP(z) (e.g., standard deviation/variance as shown in FIG. 11B) in depth. This standard deviation thresholding level is indicated in FIG. 11B at a standard deviation level.

Referring back to FIG. 5, after processing the interference signal to obtain the dynamic speckle property signal DPP(z) 512, the dynamic speckle property signal is analyzed 516 to detect dynamic speckles and to analyze their properties. For example, depth locations of dynamic speckles are indicated in FIG. 11B by large points ("○"). In other words, dynamic speckles are considered to be at depths at the location corresponding to the dynamic speckle property signal DPP(z) at which the dynamic speckle property signal DPP(z) is greater or equal to the thresholding level. If a particular structure at a given depth (or depth range) is known, the number of large points ("○") and thus the number of dynamic speckles in those structures can be determined.

Figure 12:
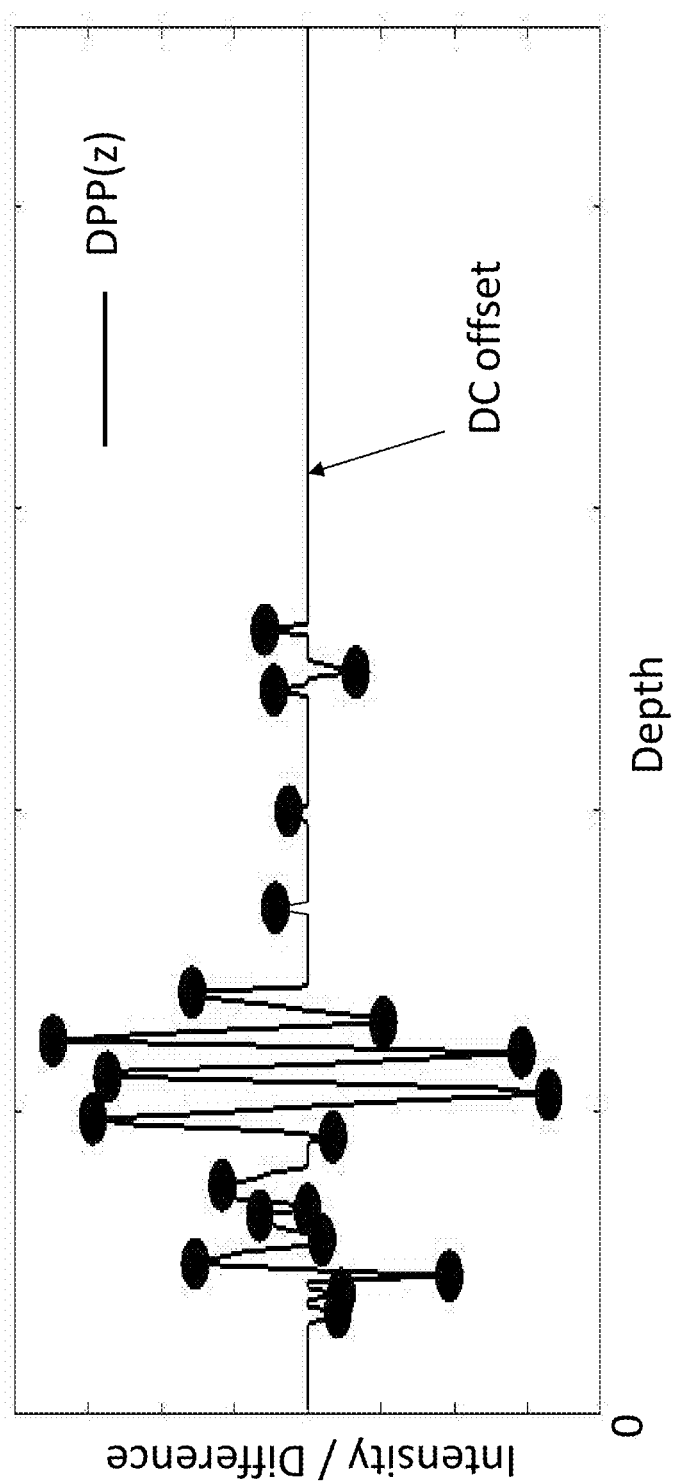
FIG. 12 illustrates the example dynamic speckle property signal DPP(z) of FIG. 10 with each peak location of the signal in depth indicated.

FIG. 12 illustrates the example dynamic speckle property signal of FIG. 10 with each peak location of the signal in depth indicated by large points ("●"). In this example, each peak represents the depth location of a dynamic speckle. These peaks, or local maxima and minima of the dynamic speckle property signal DPP(z), can be determined by any peak detection method. For example, the zero crossings of a dynamic speckle location DPL(z) (also referred to as a dynamic speckle location signal) of the dynamic speckle property signal DPP(z) correspond to peaks in DPP(z), and thus dynamic speckle locations. In other words:

$$DPL(z) = \frac{d}{dz} DPP(z)$$

Figure 13:
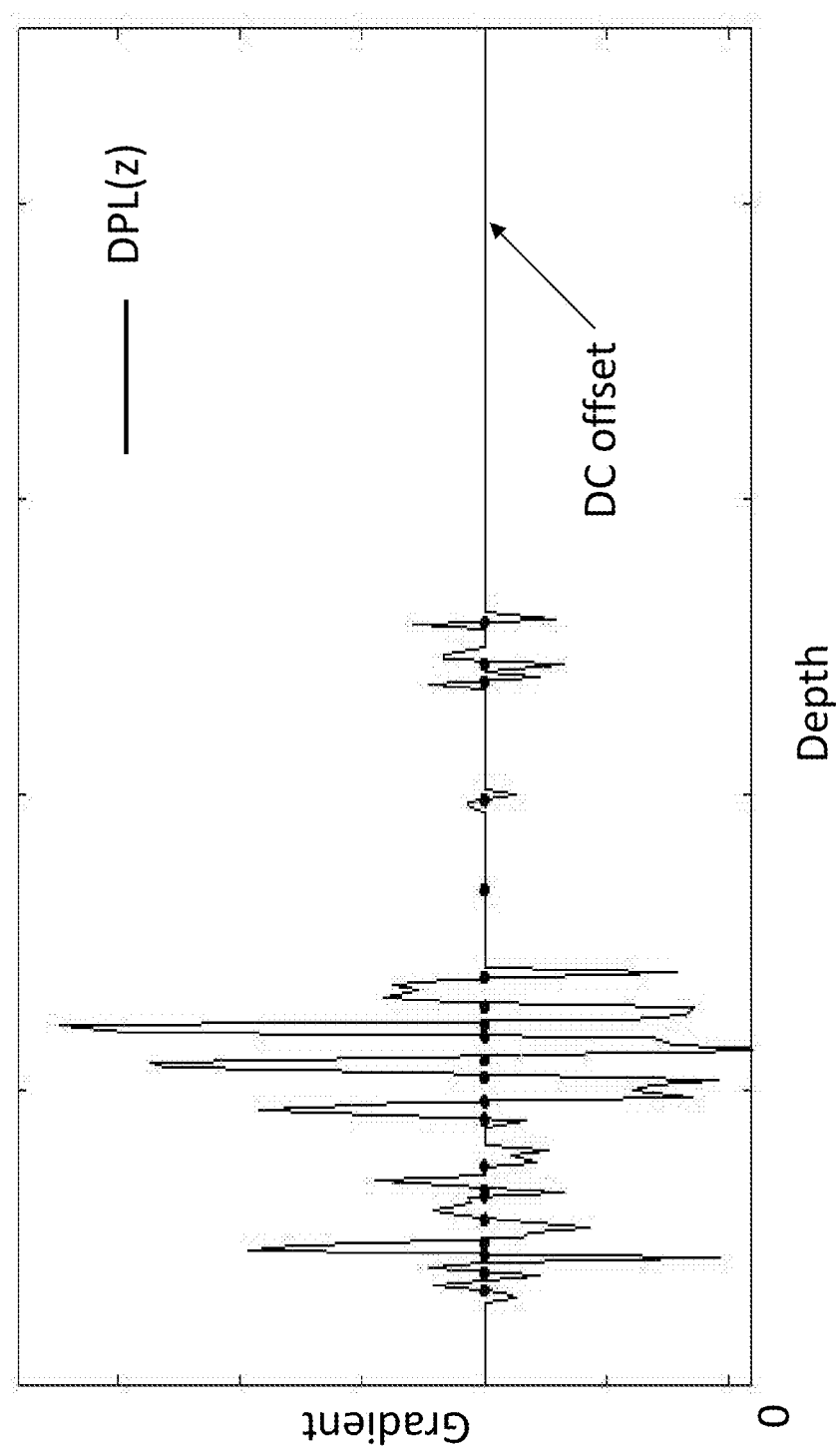
FIG. 13 illustrates an example dynamic speckle location signal DPL(z) of the example dynamic speckle property signal DPP(z) of FIG. 12, where the zero crossing depths are indicated.
Figure 14:
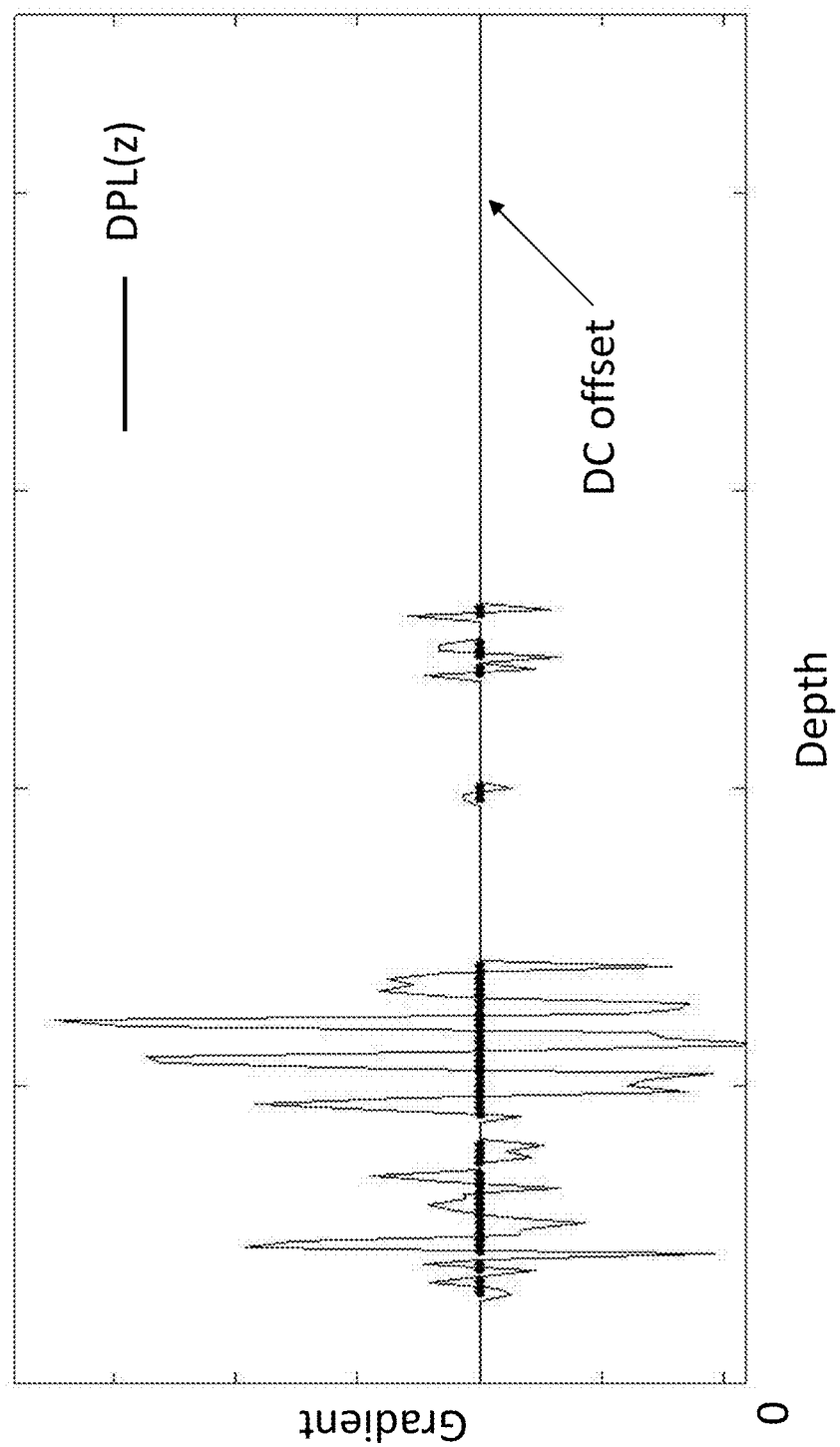
FIG. 14 illustrates an example dynamic speckle location signal DPL(z) of the example dynamic speckle property signal DPP(z) of FIG. 12, where the non-zero crossing depths are indicated.

The dynamic speckle location DPL(z) of the dynamic speckle property signal DPP(z), and the corresponding zero crossings are shown in FIG. 13. In another example, shown in FIG. 14, the non-zero difference points (or pixels) in depth are indicated by large points ("●"). The non-zero pixels in a user defined spatial and/or temporal region of interest may be counted for visualization purpose.

Figure 15:
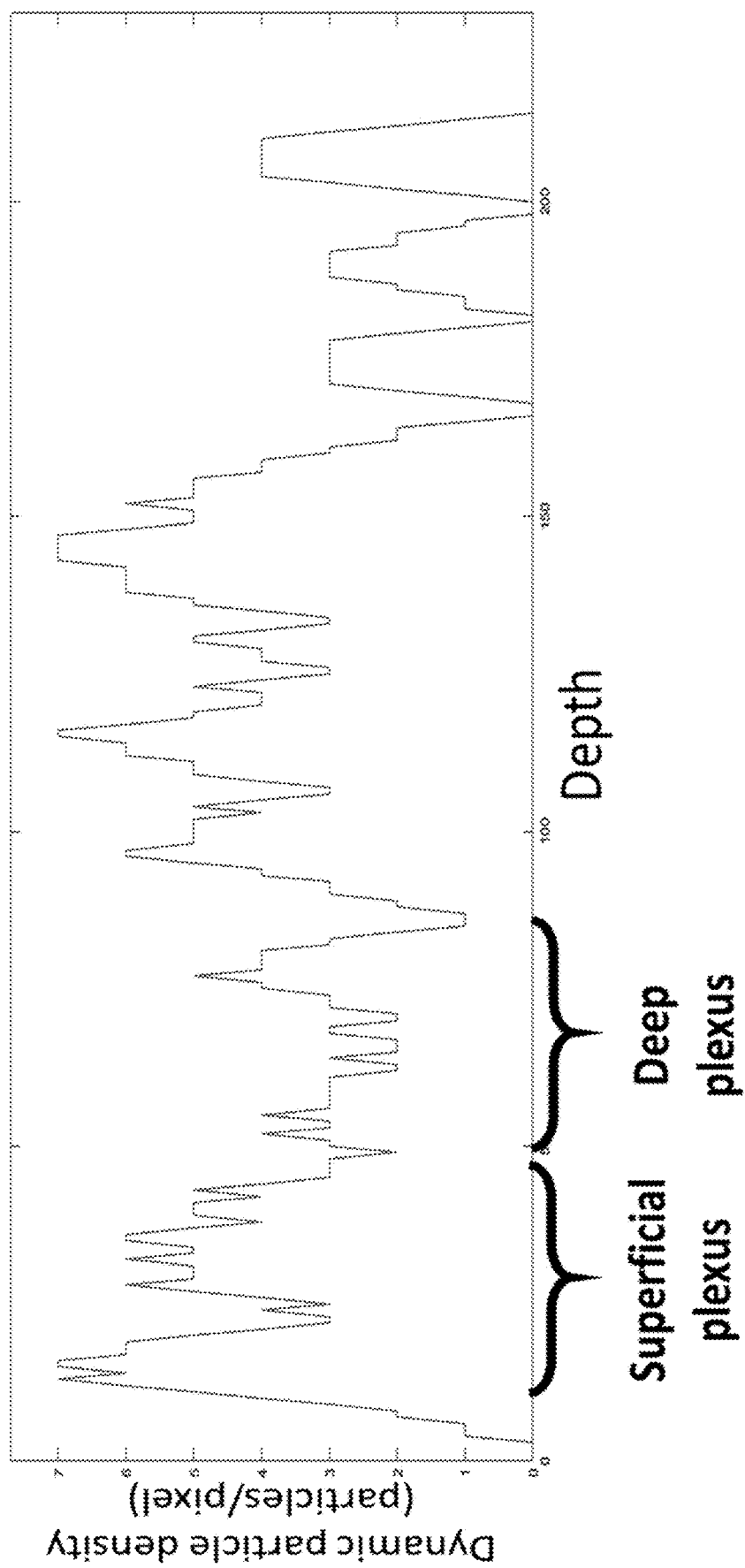
FIG. 15 illustrates a graph of dynamic speckle density.

FIG. 15 illustrates a graph of dynamic speckle density (or frequency). The dynamic speckle density is proportional to the number of dynamic speckles in a unit area, volume, time, and/or user defined space and time (e.g., a depth range). Thus a density of dynamic speckles can be measured by counting the total number of peaks at the depths of dynamic speckle property signals DPP(z) (determined as discussed above and illustrated in Fig.) within a certain boundary. The boundary may be related to particular physiological regions or structures (e.g., a retinal layer) and/or predetermined by a user. In the example of FIG. 15, dynamic speckle density is indicated as the total zero-crossing points of the dynamic speckle location DPL(z) signals for depth profiles within a user-defined kernel size (N pixel size for locations of a region of interest over given depths). As the depths of the superficial plexus and deep plexus layers are known (and indicated on the graph of dynamic speckle density), the density of each layer (and other known layers/depths) can be determined and compared. For example, it can be seen that the density of dynamic speckles is greater in the superficial plexus than in the deep plexus for the region of interest graphed in FIG. 15.

Figure 16A:
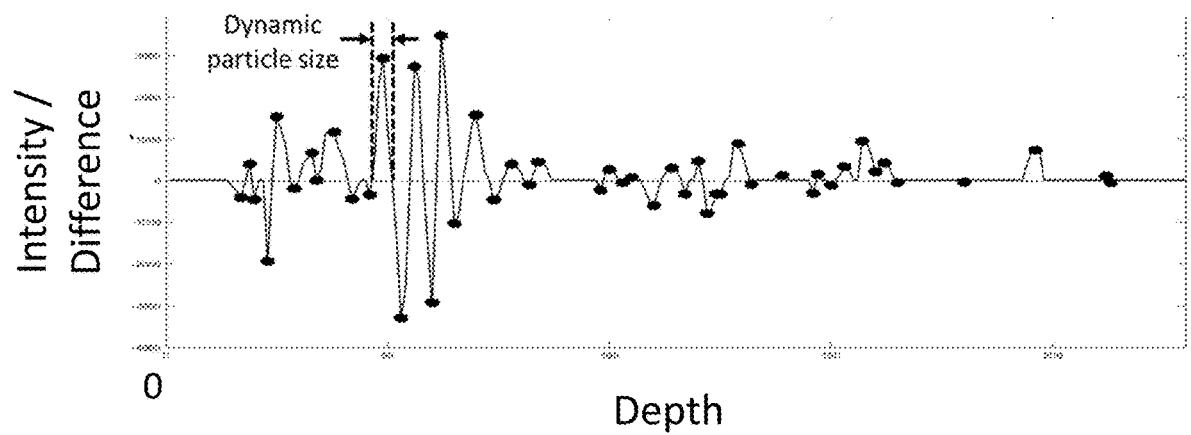
FIG. 16A illustrates the determination of dynamic speckle dimension from a dynamic speckle property signal DPP(z).
Figure 16B:
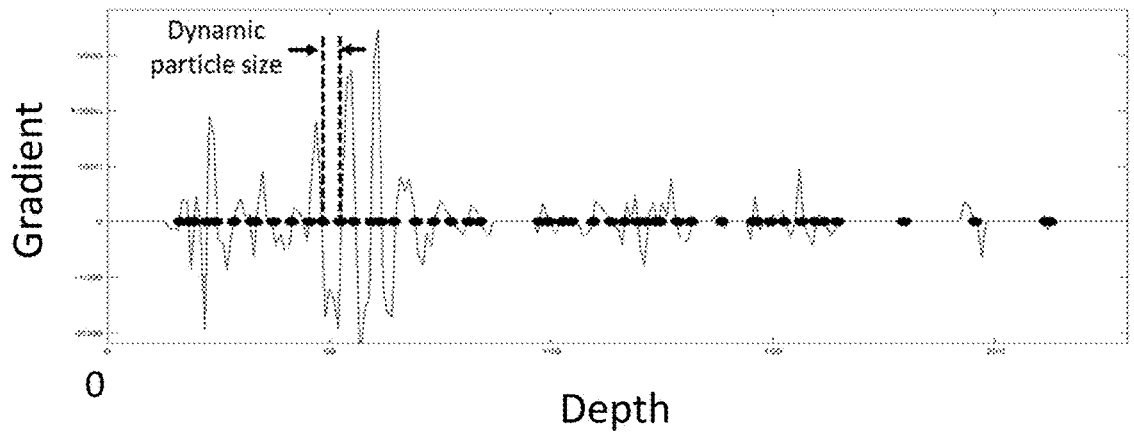
FIG. 16B illustrates the determination of dynamic speckle dimension from a dynamic speckle location signal DPL(z).
Figure 16C:
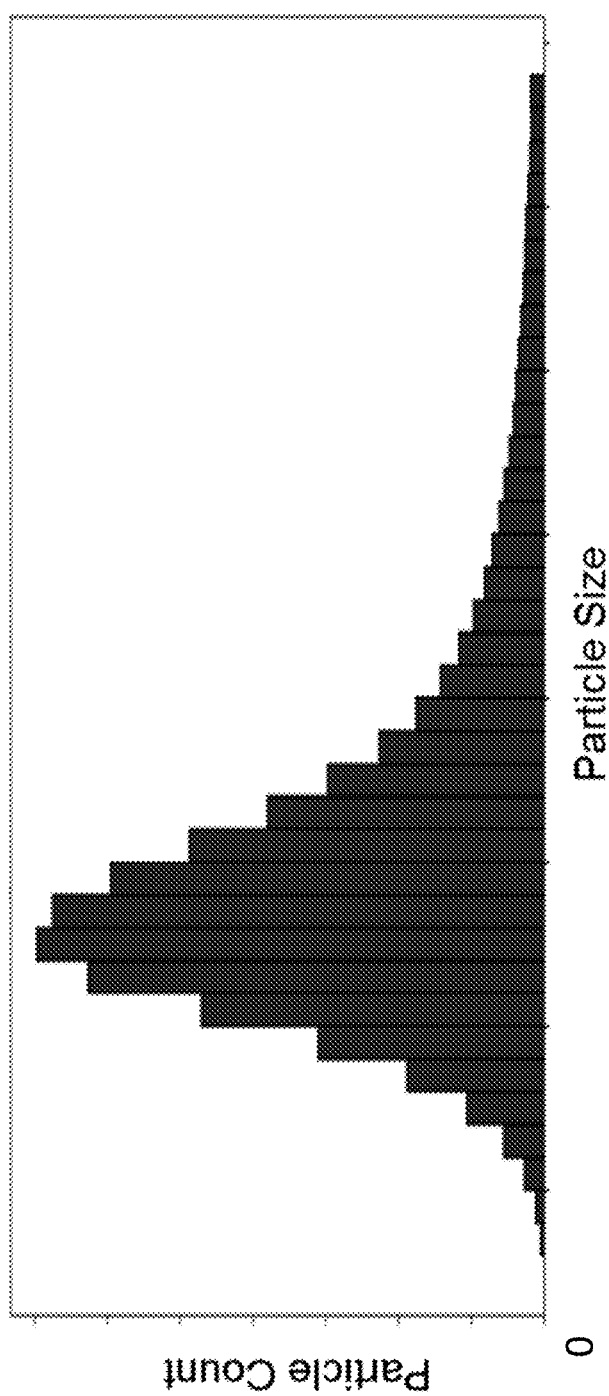
FIG. 16C illustrates an example dynamic speckle size distribution.

In still another example, dynamic speckle size can be determined from either the dynamic speckle property signal DPP(z) or the dynamic speckle location signal DPL(z). As shown in FIG. 16A, the dynamic speckle dimension is proportional to the width of each peak of the dynamic speckle property signal DPP(z). As shown in FIG. 16B, the dynamic speckle dimension is also proportional to the distance between two zero-crossing points of the dynamic speckle location signal DPL(z). With the dynamic speckle size, a distribution of dynamic speckle sizes for any region of interest, depth range, or the like, can be determined. Such an example distribution is illustrated in FIG. 16C.

Figure 17:
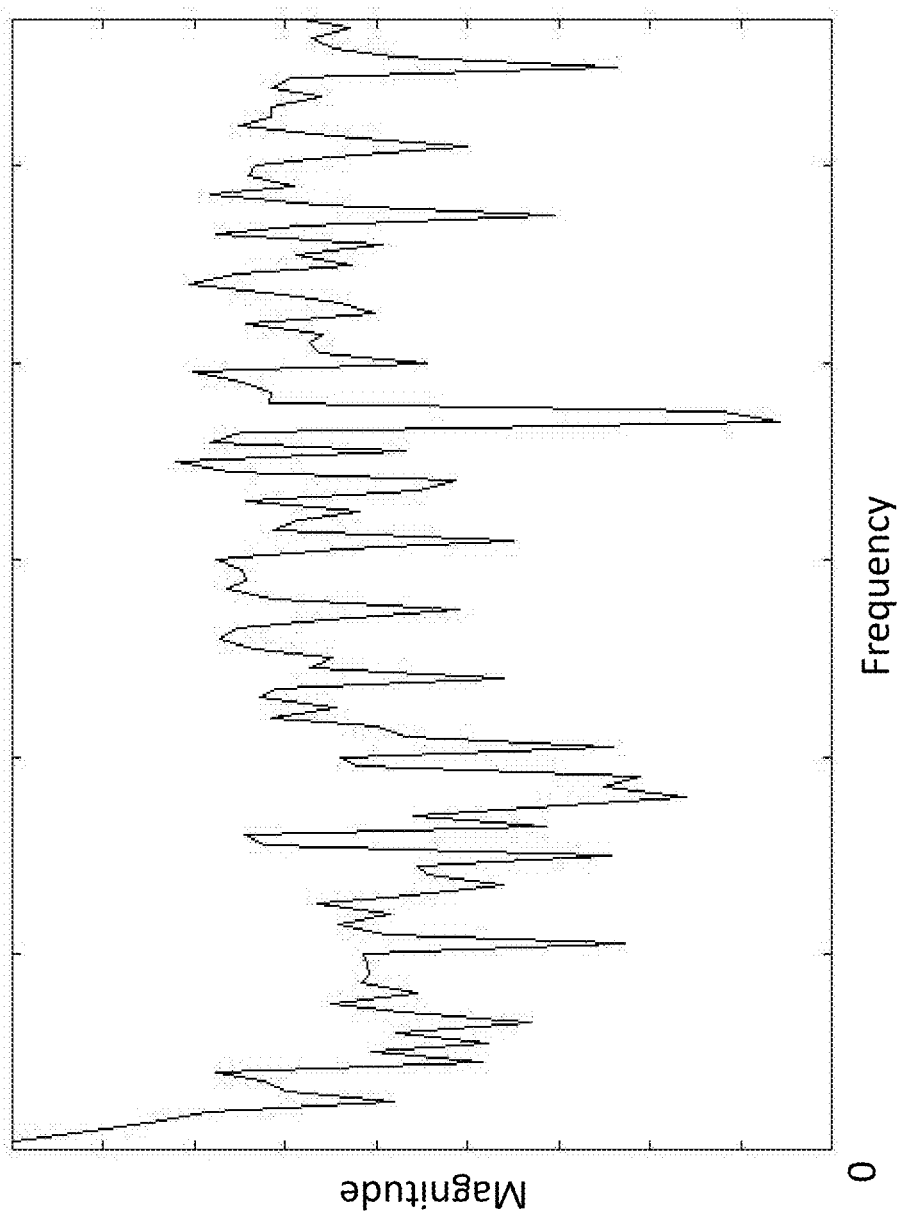
FIG. 17 illustrates an example power spectrum of the dynamic speckle location signal DPL(z) of FIG. 16B.

If it is assumed that each zero-crossing point of the dynamic speckle location signal DPL(z) represents a center point of dynamic speckle displacement, the spatial distance between adjacent zero-crossing points can mean a spacing between adjacent dynamic speckles. This spatial distribution and population of dynamic speckles can be analyzed by taking Fourier transform. Accordingly, the power spectrum of the dynamic speckle location signal DPL(z) constructed by taking the Fourier transform of dynamic speckle location signal DPL(z) can be used to analyze relative information about adjacent particles. For example, a particular frequency distribution profile may indicate microaneurysms from a diseased tissue. An example power spectrum is illustrated in FIG. 17.

Referring back again to FIG. 5, following analysis 516 of the dynamic speckle properties, the imaging data and analysis results may then be visualized 520 or otherwise presented to a user via the input/output interface, or stored 522 for later viewing and/or analysis. Such visualization may be of the entire data set and/or subsequent analysis within a user defined spatial area and/or temporal duration 518.

In one example, the visualization 520 may include generating a 2D projection image (corresponding to a C-scan or en-face image) based on processing of a plurality of A-lines according to the above description. For example, each pixel of the 2D projection image may be generated by determining (or counting) the peaks or the non-zero pixels of the dynamic speckle property signal DPP(z) or dynamic speckle location signals DPL(z) from depth profiles for each A-line within a given region of interest (the region shown in the 2D projection image). Accordingly, higher intensity pixels in the 2D projection image may correspond to more peaks or non-zero pixels within the spatial region/temporal duration of interest, and thus a greater number of speckles. Of course, intensity may instead be inversely proportional to the identified number dynamic speckles. It is noted that such 2D projection images may be projections of the entire depth profile, or depths of interest (e.g., different layers or combinations of layers of the imaged object). The images may also be within a temporal duration of interest by considering only the depth profiles (and differences/changes therebetween) taken in the time of interest.

Figure 18A:
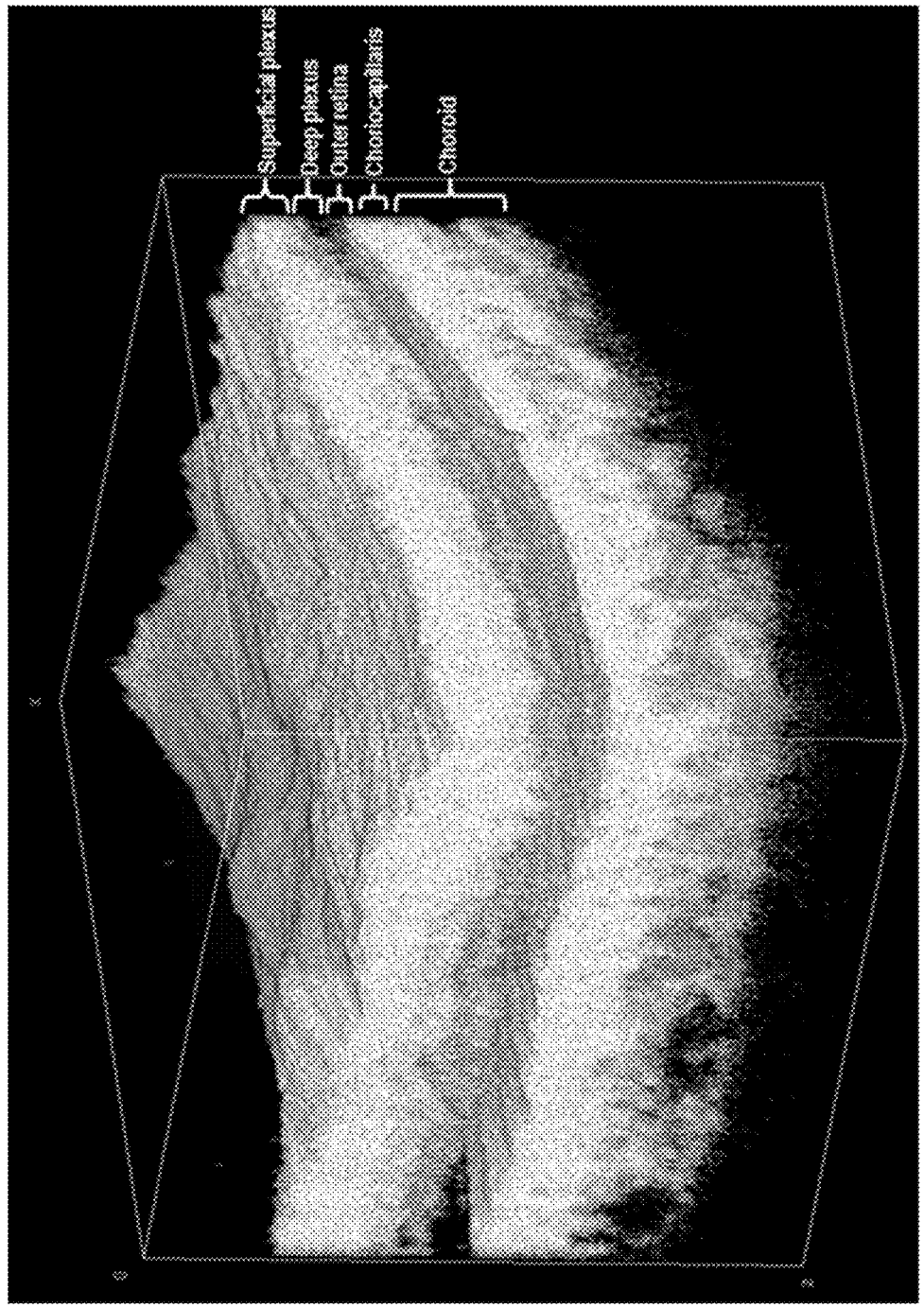
FIGS. 18A and 18B illustrate a volume of detected dynamic speckles from a 3D volume of OCT data, respectively.
Figure 18B:
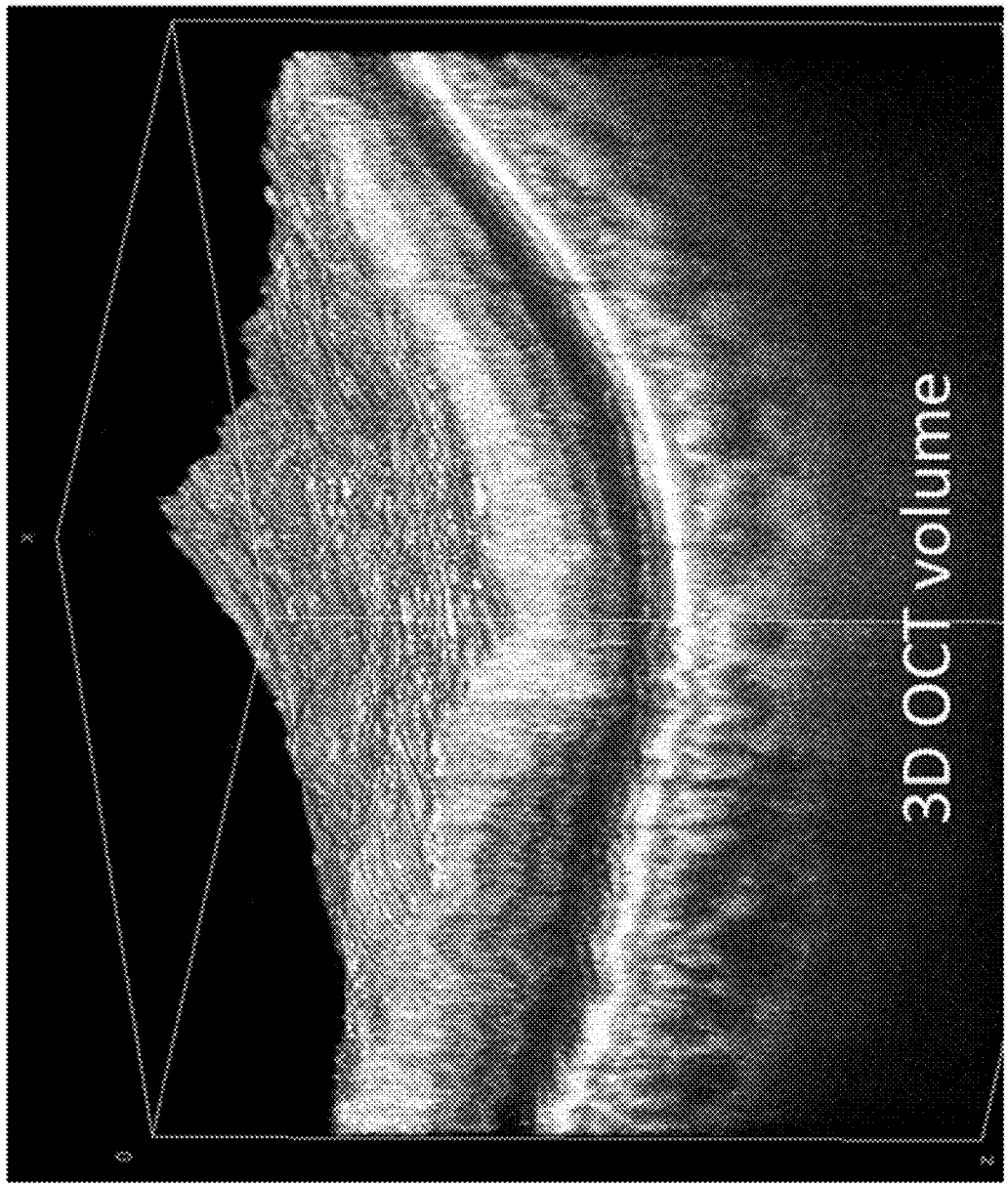

2D B-scan images (cross-sectional images including depth) can also be generated to illustrate dynamic speckles and/or their properties. For example, where each depth profile corresponds to an A-line of a B-scan, a B-scan image may be formed by setting an intensity level, for each pixel at a depth corresponding to a detected dynamic speckle, to be greater than the pixels corresponding to depths with no detected dynamic speckles. Accordingly, the locations of dynamic speckles become visible. In other embodiments, the intensity level at various pixel depths may be set to correspond to speckle properties, such as size. Accordingly, variations in dynamic speckle properties become visible. A plurality of these B-scans may then collectively form a 3D volume showing the detected dynamic speckles in the volume. FIG. 18A illustrates such a volume of detected dynamic speckles from original 3D OCT data illustrated in FIG. 18B.

Figure 19:
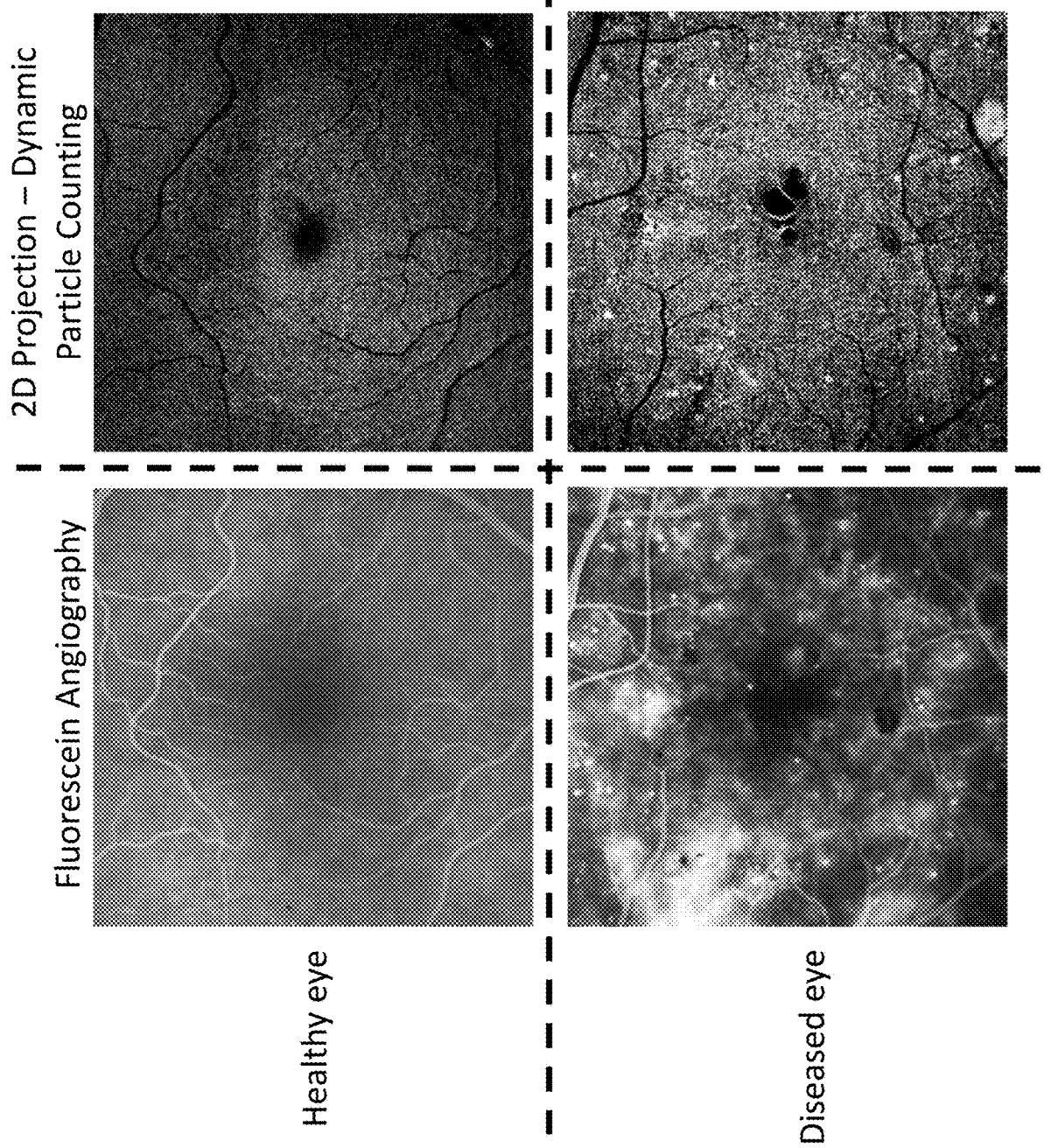
FIG. 19 illustrates a comparative view of a fluorescein angiography image and a 2D projection image based on counting dynamic speckles according to the present disclosure, for the deep plexus layer of both healthy and diseased eyes.
Figure 20:
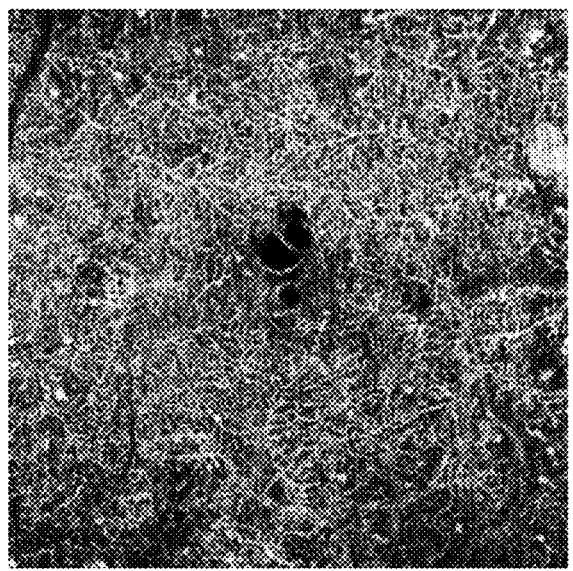
FIG. 20 illustrates a comparative view of a color fundus image, a fluorescein angiography image, and a 2D projection image based on non-zero pixel counting according to the present disclosure, for a diseased eye having microaneurysms.
Figure 20:
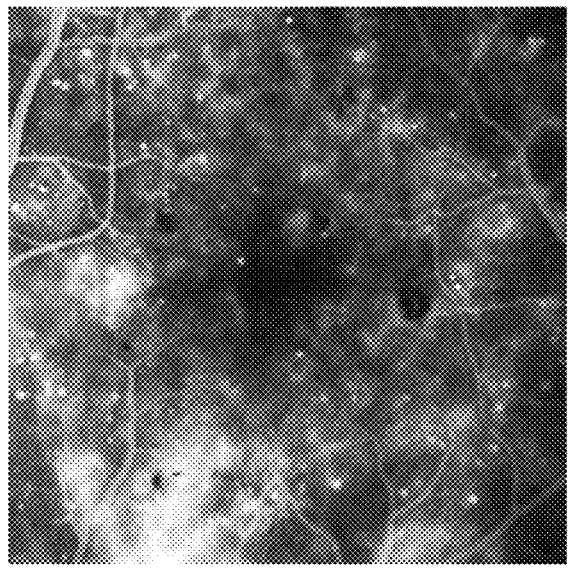
Figure 20:
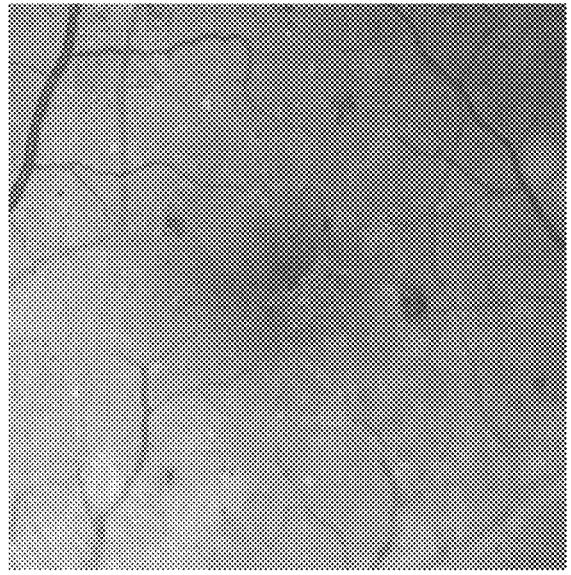

As noted above, conventional optical coherence tomography angiography (OCT-A) images are not sensitive enough to visualize microaneurysms (MA) or choroidal neovascularization (CNV). However, a 2D projection image generated by the present disclosure can provide information that is comparable to fluorescein angiography (FA), indocyanine green angiography (ICGA), and like techniques that utilize fluorescent dyes. For example, FIGS. 19 and 20 illustrate comparative views of FA and color fundus images (shown in grayscale) to 2D projection images based on the present disclosure. Particularly, FIG. 19 comparatively shows images of the deep plexus layer for both healthy and diseased human maculae generated by FA and 2D projection imaging based on counting dynamic speckles (e.g., peaks of a dynamic speckle property signal DPP(z)) as described above. FIG. 20 similarly illustrates images from a diseased eye having microaneurysms as a color fundus image, an FA image, and a 2D projection image based on non-zero pixel counting as described above. As can be seen in the diseased eye images of FIG. 19, both the FA image and the 2D projection images are capable of showing bright spots indicating the presence of microaneurysms.

Figure 21:
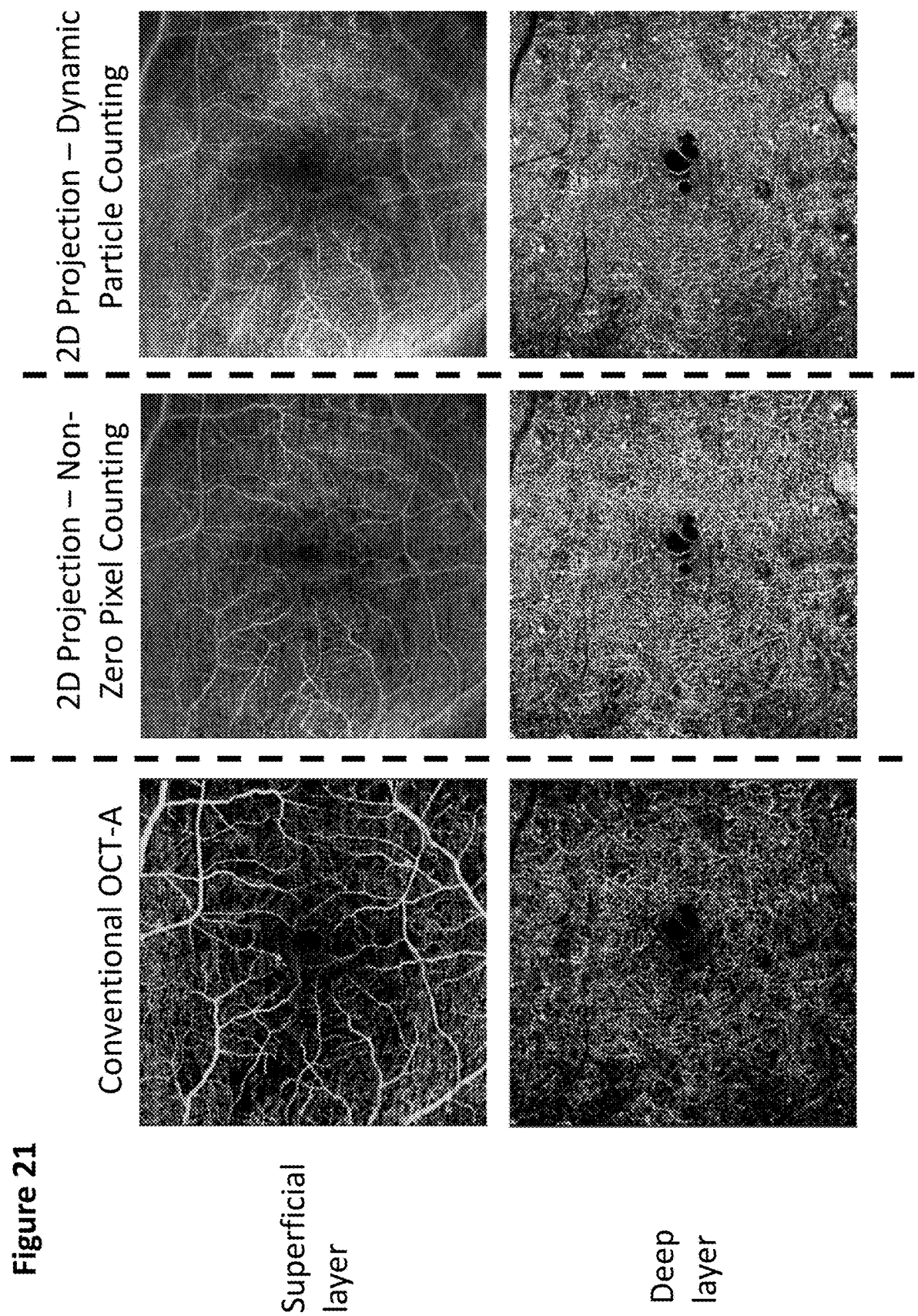
FIG. 21 illustrates a comparative view of a conventional OCT angiography image, and 2D projection images based on non-zero pixel counting and dynamic speckle counting according to the present disclosure, from the superficial and deep plexus layers for a diseased human macula.

FIG. 21 illustrates comparative views of a traditional OCT angiography image and 2D projection images formed from the present disclosure at the superficial and deep plexus layers for a diseased human macula. The 2D projection images formed based on the present disclosure were formed using the non-zero pixel counting technique, and by counting dynamic speckles (e.g., by counting technique peaks of a dynamic speckle property signal DPP(z)), across the superficial and deep layers of the maculae, as noted in the figure. As can be seen in the comparison, microaneurysms are visible in the 2D projections while the OCT-A images are not sensitive enough for them to be identified.

Figure 22:
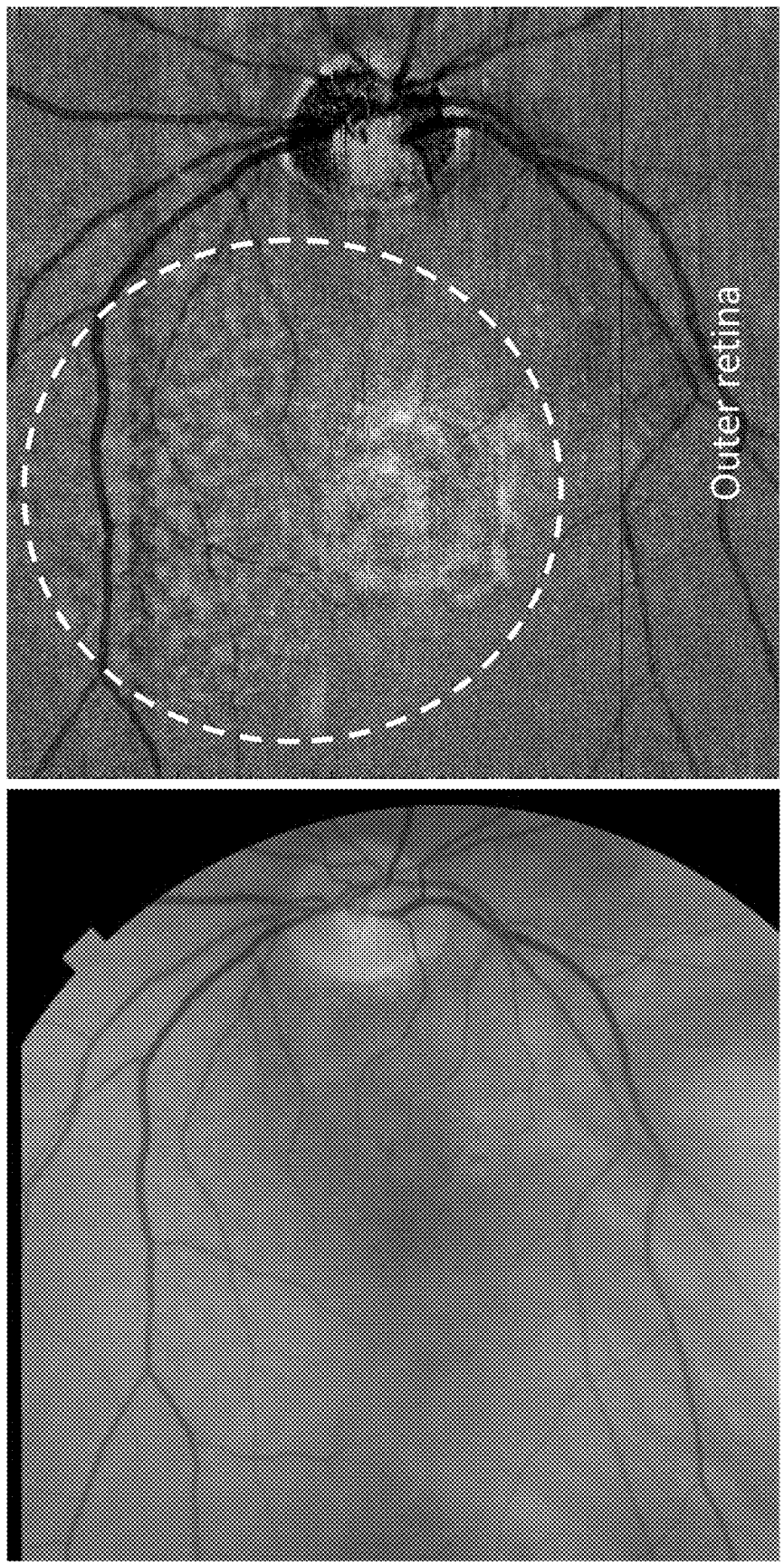
FIG. 22 illustrates a comparative view of a color fundus image and a 2D projection image based on counting dynamic speckles according to the present disclosure, of a human outer retina having choroidal neovascularization.

FIG. 22 illustrates comparative views of a color fundus image (shown in grayscale) and a 2D projection image based on counting dynamic speckles (e.g., by counting technique peaks of a dynamic speckle property signal DPP(z)) according to the present disclosure, of a human outer retina. The presence of choroidal neovascularization (circled in white in the 2D projection image) is visible in the 2D projection image.

It is further noted that any of the visualizations according to the present disclosure may be colorized, for example, by applying color based on predetermined pixel intensity thresholds. Such colorization may be used, for example, to highlight microaneurysms (e.g., in a blue color). Such colorization may make abnormalities even more identifiable in the visualizations.

Finally, as noted above and shown in FIG. 5, any of the above data—acquired or resulting from processing—and the associated images may be stored 522 for later analysis for visualization. These data and images may be stored at the imaging system or remotely, for example, within the database of the system as shown in FIG. 4.

The present disclosure of a low coherence interferometry system and method is not limited to the above described benefits and applications. For example, the present disclosure can be used for eye disease detection in ophthalmology, providing information comparable to FA and/or ICGA images, blood vessel visualization without fluorescent dye injection, blood vessel leakage visualization without fluorescent dye injection, visualization of diseased area such as microaneurysm (MA), choroidal neovascularization (CNV), hemorrhage, subretinal fluid region, and the like. The present disclosure may also be used in diagnosis of specific diseases, including but not limited to, diabetic retinopathy, age related macular degeneration, macular telangiectasia, polypoidal choroidal vasculopathy, glaucoma and optic neuropathies, retinitis pigmentosa, retinal vascular occlusion, and the like. Additionally, while the present disclosure has been presented as an application for ophthalmological imaging, it is not limited thereto. For example, the present disclosure can be applied to cancer detection in oncology, skin disease detection in dermatology, brain disease detection in neurology, cardiovascular disease detection in cardiology, non-destructive evaluation and non-destructive testing fields, cell monitoring in biology, and the like. Additionally, other conventional OCT-A processing methods, such as optical coherence tomography angiography ratio analysis (OCTARA), split-spectrum amplitude-decorrelation angiography (SSADA), optical microangiography (OMAG), and other OCT angiography processing methods can be adapted according to the present disclosure to provide features similar to those discussed herein.

What is claimed is:
1. An imaging method comprising:
acquiring an image data set of an object with an interferometric imaging system, wherein the image data set comprises image data from a location of the object at a first time and at a second time;
determining a first depth profile from the image data from the location at the first time and a second depth profile from the image data of the location at the second time;
determining a change with respect to depth between the first depth profile and the second depth profile;
identifying depths of the object at which the change between the first depth profile and the second depth profile is at a local maxima or minima; and
determining a property, or identifying a location, of at least one dynamic particle in the object based on the identified local maxima or minima,
wherein the identified depths at which the change is at the local maxima or minima correspond to locations of dynamic particles; and
wherein the object is a human eye.
2. The method of claim 1, further comprising:
generating an image of the object based on the at least one determined dynamic particle property, and
displaying the image.

3. The method of claim 2, further comprising:
applying a threshold to the change between the first depth profile and the second depth profile prior to generating the image.

4. The method of claim 3, wherein the threshold is:
proportional to a noise floor of the interferometric imaging system,
determined from a histogram of a difference level of the change between the first depth profile and the second depth profile, or
is proportional to a frame size and/or sample size of the image data.

5. The method of claim 1, wherein the first depth profile or the second depth profile is in the complex domain.

6. The method of claim 1, wherein a light source of the interferometric imaging system is a low coherence light source.

7. The method of claim 1, wherein the change is a difference between the first depth profile and the second depth profile, or an absolute value of the difference.

8. The method of claim 1, wherein the change is a ratio between the first depth profile and the second depth profile, or an absolute value of the ratio.

9. The method of claim 1, wherein the change is a correlation or decorrelation between the first depth profile and the second depth profile.

10. The method of claim 1, wherein the change is a standard deviation or variance between the first depth profile and the second depth profiles.

11. The method of claim 1, further comprising:
determining a first derivative of the change between the first depth profile and the second depth profile; and
identifying depths of the object at which the first derivative is zero,
wherein the identified depths at which the first derivative is zero correspond to locations of dynamic particles.

12. The method of claim 1, further comprising:
determining a first derivative of the change between the first depth profile and the second depth profile; and
identifying depths of the object at which the first derivative is not zero,
wherein the property of the at least one dynamic particle is based on a number of identified depths at which the first derivative is not zero.

13. The method of claim 1, further comprising:
applying a threshold to the first depth profile and/or the second depth profile prior to determining the change between the first depth profile and the second depth profile.

14. The method of claim 13, wherein the threshold is:
proportional to a noise floor of the interferometric imaging system,
determined from a histogram or a cumulative histogram of an intensity of the first depth profile or the second depth profile, or
is proportional to a frame size and/or sample size of the image data.

15. The method of claim 1, wherein the image data set is 3D optical coherence tomography data.

16. The method of claim 1, wherein the determined property is a dynamic particle density, and the dynamic particle density is determined as the total number of identified locations of dynamic particles over a predefined depth within a region of interest.

17. The method of claim 1,
wherein the determined property is a size of the at least one dynamic particle, and
wherein the size is proportional to a width of the local maxima or minima peak of the change between the first depth profile and the second depth profile, or to a distance between depths at which a first derivative of the change between the first depth profile and the second depth profile is zero.

18. The method of claim 17, further comprising determining a dynamic particle size distribution based on the determined sizes.

19. The method of claim 1, further comprising determining a power spectrum of a first derivative of the change between the first depth profile and the second depth profile.

* * * * *